(12) United States Patent
Lomholt et al.

(10) Patent No.: US 7,504,495 B2
(45) Date of Patent: Mar. 17, 2009

(54) QUENCHER COMPOSITIONS COMPRISING ANTHRAQUINONE MOIETIES

(75) Inventors: Christian Lomholt, Frederiksberg C (DK); Henrik M. Pfundheller, Horsholm (DK); Michael Meldgaard, Hillerod (DK)

(73) Assignee: Exiqon A/S, Vedbaek (DK)

( * ) Notice: Subject to any disclaimer, the term of this patent is extended or adjusted under 35 U.S.C. 154(b) by 330 days.

(21) Appl. No.: 10/993,994

(22) Filed: Nov. 19, 2004

(65) Prior Publication Data

US 2005/0227254 A1 Oct. 13, 2005

(30) Foreign Application Priority Data

Nov. 20, 2003 (DK) ............... 2003 01723

(51) Int. Cl.
*C07H 21/02* (2006.01)
*C07H 19/04* (2006.01)
*C12Q 1/68* (2006.01)
*C07D 265/34* (2006.01)
*C07C 46/00* (2006.01)

(52) U.S. Cl. .................. 536/26.6; 536/23.1; 435/6; 544/100; 552/268

(58) Field of Classification Search ................ 536/23.1, 536/26.6, 16.6; 435/6; 544/100; 552/268
See application file for complete search history.

(56) References Cited

U.S. PATENT DOCUMENTS

| | | | |
|---|---|---|---|
| 5,118,934 | A | 6/1992 | Hailey et al. |
| 5,188,934 | A | 2/1993 | Menchen et al. |
| 5,366,860 | A | 11/1994 | Bergot et al. |
| 5,800,996 | A | 9/1998 | Lee et al. |
| 5,847,162 | A | 12/1998 | Lee et al. |
| 5,863,727 | A | 1/1999 | Lee et al. |
| 5,936,087 | A | 8/1999 | Benson et al. |
| 5,945,526 | A | 8/1999 | Lee et al. |
| 6,008,379 | A | 12/1999 | Benson et al. |
| 6,020,481 | A | 2/2000 | Benson et al. |
| 6,051,719 | A | 4/2000 | Benson et al. |
| 6,127,121 | A | 10/2000 | Meyer, Jr. et al. |
| 6,140,500 | A | 10/2000 | Yan et al. |
| 6,143,877 | A | 11/2000 | Meyer et al. |
| 6,191,278 | B1 | 2/2001 | Lee et al. |
| 2003/0096254 | A1 | 5/2003 | Reed et al. |
| 2004/0110308 | A1 | 6/2004 | Laikhter et al. |

FOREIGN PATENT DOCUMENTS

| | | |
|---|---|---|
| WO | WO 97/45539 | 12/1997 |
| WO | WO 98/22489 | 5/1998 |
| WO | WO 98/39352 | 9/1998 |
| WO | WO 99/14226 | 3/1999 |
| WO | WO 01/38584 | 5/2001 |
| WO | WO 2004/026804 | 4/2004 |

OTHER PUBLICATIONS

Andrus, A. "Chemical methods for 5' non-isotopic labelling of PCR probes and primers" in PCR 2: A Practical Approach, Oxford University Press, Oxford, pp. 39-54 (1995).

Barasch et al.: "Novel anthraquinone derivatives with redox-active functional groups capable of producing free radicals by metabolism: are free radicals essential for cytotoxicity?" *Eur J Med Chem.* 34:597-615 (1999).

Beaucage and Caruthers, "Deoxynucleoside Phosphoramidites—A New Class of Key Intermediates for Deoxypolynucleotide Synthesis," *Tetrahedron Lett.* 22: 1859-1862 (1981).

Fasman in Practical Handbook of Biochemistry and Molecular Biology, pp. 385-394, CRC Press, Boca Raton, Florida (1989).

Förster, "Zwischenmolekular Energiewanderung und Fluoreszenz," *Ann Phys.* 2:55-75 (1948).

Fujimori, "Enantio-DNA Recognizes Complementary RNA but Not Complementary DNA," *J Amer Chem Soc.* 112:7436-8 (1990).

Garbesi, "L-DNAs as potential antimessenger oligonucleotides: a reassessment," *Nuci Acids Res.* 21:4159-65 (1993).

Gibson et al..: "Molecular modelling of anthraquinone-oligodeoxynucleotide conjugates" *Pharmaceutical Sciences* 2:545-548 (1996).

Johansson et al, "Intramolecular Dimers: A New Strategy to Fluorescence Quenching in Dual-Labeled Oligonucleotide Probes," *J Am Chem Soc.* 124:6950-6956 (2002).

Johansson and Cook, "Intramolecular Dimers; A New Design Strategy for Fluorescence-Quenched Probe," *Chem Eu. J.* 9:3466-3471 (2003).

Kricka, L.Nucleic Acid Hybridization Test Formats:Strategies and Applications, in Nonisotopic DNA Probe Techniques, Academic Press, San Diego, pp. 3-28 (1992).

Marras et. al., "Efficiencies of flourescence resonance energy transfer and contact-mediated quenching in oligonucleotide probes," *Nucleic Acid Res.* 30:e122 (2002).

May et. al., "A new dark quencher for use in genetic analysis," *Chem Commun.* 970-971 (2003).

Miyashita et al., "Novel dinucleoside phosphotriester unit conjugated with an intercalative moiety in a stereospecific manner enhances thermal stability of an alternate-stranded triple helix," *Tetrahedron Lett.* 44(40): 7399-7402 (2003).

(Continued)

*Primary Examiner*—Jezia Riley
(74) *Attorney, Agent, or Firm*—Clark & Elbing, LLP; Kristine Bieker-Brady

(57) ABSTRACT

The present invention provides novel quencher composition comprising anthraquinone quencher moieties. The anthraquinone quencher moieties are useful as quencher labels when attached to biomolecules such as natural or modified polynucleotides, oligonucleotides, nucleosides, nucleotides, carbohydrates and peptides. For example, polynucleotides can be labeled at the 3' terminus with fluorescence quencher solid support compositions, and polynucleotides can be labeled at internally or at the 5' terminus. The detectable probes may have a format like molecular beacons, scorpion probes, sunrise probes, conformationally assisted probes and TaqMan probes.

4 Claims, 10 Drawing Sheets

OTHER PUBLICATIONS

Sinha et al., "β-Cyanoethl N, N-Dialkylamino/N-Morpholinomonochloro Phosphoamidites, New Phosphitylating Agents Facilitating Ease of Deprotection and Work-up of Synthesized Oligonucleotides," *Tetrahedron Lett*. 24:5843-5846 (1983).

Still et al., "Rapid Chromatographic Technique for Preparative Separations with Moderate Resolution," *J Org Chem*. 43(14): 2923-25 (1978).

Urata, "Spectroscopic characterization of heterochiral DNAs," Nucleic Acids Symposium Ser. No. 29:69-70 (1993).

Beaucage and M.H. Caruthers, Chapter 3.3 and Chapter 4 in Current Protocols in Nucleic Acid Chemistry, John Wiley & Sons, Inc., (1999).

Blackburn, G. and Gait, M. Eds., "DNA and RNA Structure", in Nucleic Acids in Chemistry and Biology, 2nd Edition, Oxford University Press, pp. 15-81, (1996).

Spatola, A.F., in Chemistry and Biochemistry of Amino Acids, Peptides and Proteins, B. Weinstein, Ed., Marcel Dekker, New York, p. 267 (1983).

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Synthetic probe

<400> SEQUENCE: 1
cgcgtttact ttgaaaaatt ctg                                            23

<210> SEQ ID NO 2
<211> LENGTH: 20
<212> TYPE: DNA
<213> ORGANISM: Artificial Sequence
<220> FEATURE:
<223> OTHER INFORMATION: Synthetic probe

<400> SEQUENCE: 2
gcttccaatt tcctggcatc                                                20

<210> SEQ ID NO 3
<211> LENGTH: 24
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<222> LOCATION: 1
<223> OTHER INFORMATION: Derivatized with fluoroscein at 5'
<220> FEATURE:
<221> NAME/KEY: misc_feature
<222> LOCATION: 24
<223> OTHER INFORMATION: Derivatized with anthraquinone at 3'
```

```
<400> SEQUENCE: 3
tcaaggagaa ggtgggtgaa gagg                                           24

<210> SEQ ID NO 4
<211> LENGTH: 35
<212> TYPE: DNA
<213> ORGANISM: Saccharomyces cerevisiae

<400> SEQUENCE: 4
acgtgagctc attgaaactg caggtggtat tatga                               35

<210> SEQ ID NO 5
<211> LENGTH: 44
<212> TYPE: DNA
<213> ORGANISM: Saccharomyces cerevisiae

<400> SEQUENCE: 5
gatccccggg aattgccatg ctaatcaacc tcttcaaccg ttgg                     44

<210> SEQ ID NO 6
<211> LENGTH: 50
<212> TYPE: DNA
<213> ORGANISM: Artificial Sequence
<220> FEATURE:
<223> OTHER INFORMATION: Synthetic probe

<400> SEQUENCE: 6
acgtggatcc tttttttttt tttttttttt gatccccggg aattgccatg               50

<210> SEQ ID NO 7
<211> LENGTH: 20
<212> TYPE: DNA
<213> ORGANISM: Artificial Sequence
<220> FEATURE:
<223> OTHER INFORMATION: Synthetic probe

<400> SEQUENCE: 7
gtggtcgaaa gcaatggact                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic probe

<400> SEQUENCE: 8
gggattcgaa cccttggtat                                                20

<210> SEQ ID NO 9

<400> SEQUENCE: 9

000

<210> SEQ ID NO 10
<211> LENGTH: 79
<212> TYPE: DNA
<213> ORGANISM: Artificial Sequence
<220> FEATURE:
<223> OTHER INFORMATION: Synthetic probe
```

```
<400> SEQUENCE: 10
gtggtcgaaa gcaatggact tgcaggagga gcagaggaaa gaggcagaag gagaagccca        60
taccaagggt tcgaatccc                                                     79
```

QUENCHER COMPOSITIONS COMPRISING ANTHRAQUINONE MOIETIES

CROSS-REFERENCE TO RELATED APPLICATION

This application claims priority under 35 U.S.C. § 119 to Danish patent application PA 2003 01723, filed Nov. 20, 2003.

FIELD OF THE INVENTION

The present invention provides new quencher compositions, including anthraquinone quencher moieties that are useful as quencher labels when attached to biomolecules such as natural or modified polynucleotides, nucleosides, nucleotides, carbohydrates and peptides.

Also provided are methods of using the quencher compositions as probes and methods of using the probes.

BACKGROUND OF THE INVENTION

The intensity of fluorescence can be decreased by a wide variety of processes overall called quenching. For probes with a stem structure, e.g. molecular beacons and scorpion probes, or other pair of probes, e.g. kissing probes and competitive hybridisation probes, where the reporter dye and quencher are brought into close proximity, the main mechanism of quenching is static or contact quenching where the energy from the fluorophore reporter dye is transferred to the quencher which then dissipates the energy as heat without fluorescence (J. R. Lakowicz, Principles of fluorescence spectroscopy, 1999, Kluwer Academic/Plenum Publishers, New York). Static quenching occurs through the formation of a ground state complex where the reporter dye and quencher moieties bind together to form a ground state complex—an intramolecular dimer. Förster resonance energy transfer (FRET or RET) is the mechanism which commonly is cited as controlling fluorescence quenching in probes without a stem structure, e.g. TaqMan probes (Marras et. al., Nucleic Acid Res., 2002, 30, e122). FRET is a process that occurs whenever the emission spectrum of a fluorophore overlaps with the absorption spectrum of the acceptor molecule e.g. the quencher (J. R. Lakowicz, ibid.). For optimal FRET quenching the reporter and quencher moieties should be chosen so the spectral overlap between the emission fluorescence and the quencher absorption is optimal. The efficiency of the process is dependent on $1/r^6$ (Förster distance) where r is the fluorophore—quencher distance (T. Förster, Ann. Phys., 1948, 2, 55). In another collisional quenching mechanism (Dexter quenching) the excited state fluorophore is deactivated during a diffusive encounter with the quencher. Traditionally, dual-labelled probes have been designed focusing on choosing a matched fluorophore—quencher pair for optimal FRET quenching. It has recently been proposed that fluorophore—quencher pairs in non-stem dual labelled probes also should be chosen for increasing static quenching through the formation of the ground-state complex—the intramolecular dimer—as this was found to be an extremely effective quenching method (Johansson et al, J. Am. Chem. Soc., 2002, 124, 6950-6956; Johansson and Cook, Chem. Eur. J., 2003, 9, 3466-3471). Thus, fluorophore—quencher pairs with an inherent affinity of each other are suited for ground-state complex formation resulting potentially in increased quenching. Quenchers can be fluorescent e.g. TAMRA (tetramethylrhodamine) or non-fluorescent e.g. derivatives of 4-(dimethylamino)azobenzene (Dabcyl). Non-fluorescent quenchers are also referred to as dark quenchers. Fluorescent quenchers have 2 significant limitations: The presence of background fluorescence and the preclusion of detection of reporter fluorescence at the acceptor fluorescence emission. Thus, preferred quenchers are dark quenchers.

1,4-Diaminoanthraquinones have earlier been incorporated into oligodeoxynucleotides using phosphoramidite chemistry. The 1,4-diaminoanthraquinone dark quencher LQ1 ("LQ1") was incorporated into the 5'-end of DNA molecular beacons (May et. al., Chem. Commun., 2003, 970-971) with either FAM or Cy5 as a fluorophore. The LQ1 quencher has an absorption range of 500-700 nm and is thus better suited as a quencher for long wavelength dyes like Cy5 compared to other non-anthraquinone quenchers as e.g. dabcyl which on the contrary is more suited for shorter wavelength dyes like e.g. FAM. A structurally related 1,4-diaminoanthraquinone dark quencher called IOWA Black-3.1™ ("IOWA Black") is available from integrated DNA Technologies (www.idtdna.com). IOWA Black contains an α-aminoaryl group compared to an α-aminoalkyl group in LQ1 thus having a higher extinction cooefficient at higher wavelength compared to LQ1. The LQ1 and IOWA Black phosphoramidite quenchers can only be incorporated at the 5'-end of oligonucleotides when using standard phosphoramidite chemistry on DNA synthesizers and thus cannot be incorporated in the preferred 3'-end of or internally in oligonucleotide molecules. May et al. (Chem. Commun., 2003, 970-971) has prepared the 1,4-diaminoanthraquinone dark quencher molecule LQ2 which was attached to controlled pore glass (CPG) via an amide containing linker and a deoxyribose sugar. With this approach the 1,4-diaminoanthraquinone dark quencher molecule LQ2 can be incorporated into the 3'-end but not internally nor in the 5'-end of the oligonucleotide molecule. When LQ2 modified oligonucleotides are deprotected after oligonucleotide synthesis using standard deprotection conditions (concentrated aqueous ammonia) the LQ2 molecule is cleaved from the oligonucleotide due to the labile amide bonds in the linker. Alternatively, LQ2 modified oligonucleotides can be deprotected using water:methanol:tert-butylamine (2:1:1) or ammonium hydroxide:concentrated aqueous methylamine (1:1) mixtures where the use of the latter mixture results in the cleanest product. However, these procedures require either the use of N-DMF protected G phosphoramidites or N-acetyl protected C phosphoramidites, respectively, e.g. nucleoside phosphoramidites containing non-standard protecting groups.

In summary, there is a need for α-amino substituted anthraquinone dark quenchers that can be easily synthesized, are inexpensive and are capable of being incorporated internally as well as in the 3'-end and 5'-end of oligonucleotide molecules.

Furthermore, a series of quenchers having similar physical properties for e.g. increased static quenching through ground-state complex formation, but distinct spectral properties would be particular advantageous.

WO 2004/026804 A1 was filed before, but was published after, the priority date of the present application. WO 2004/026804 A1 discloses various anthraquinone quencher dyes, their preparation and use.

BRIEF DESCRIPTION OF THE INVENTION

The present invention provides quencher compositions of the formula (II), cf. claim 2.

The present invention further provides quencher compositions of the formula (III), cf. claims 1 and 2.

The present invention also provides novel, α-amino substituted anthraquinone compounds, in particular mono-, di-, tri- and tetra-α-amino substituted anthraquinone compounds.

The anthraquinone compounds are useful as quencher labels when attached to biomolecules such as natural or modified polynucleotides, nucleosides, nucleotides, carbohydrates and peptides. The anthraquinone compounds are useful for labelling when attached to biomolecules, in particular for the use as quencher labels.

The present invention further provides microarrays, methods for probing a microarray, labelled nucleosides and nucleotides, methods for labelling polynucleotides, methods for primer extension, methods for oligonucleotide ligation, methods for hybridization detection, a kit for primer extension.

The quencher labeled biomolecules may further contain fluorescent reporter moieties, which form energy transfer pairs.

Other aspects of the invention include methods of labeling polynucleotides and polypeptides with the di, tri or tetra-α-amino anthraquinone quencher moieties of the invention. For example, polynucleotides can be labeled at the 3' terminus with fluorescence quencher solid support compositions. Polynucleotides can be labeled at internally or at the 5' terminus with a di, tri or tetra-a-amino anthraquinone quencher phosphoramidite.

DETAILED DESCRIPTION OF THE INVENTION

Figure 1:
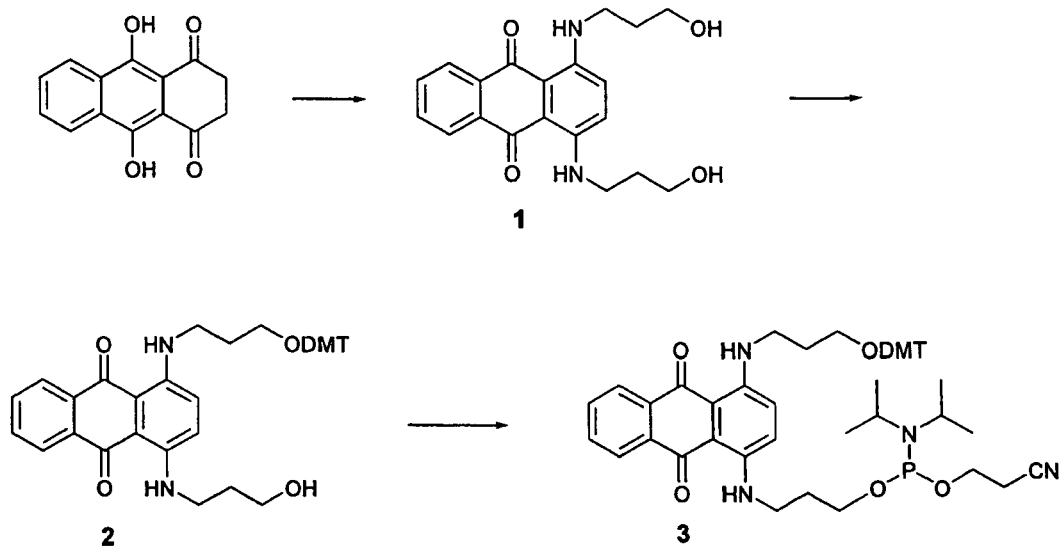
FIGS. 1-9 illustrate the synthetic routes for various quenchers as described in more detail in the Examples section.
Figure 2:
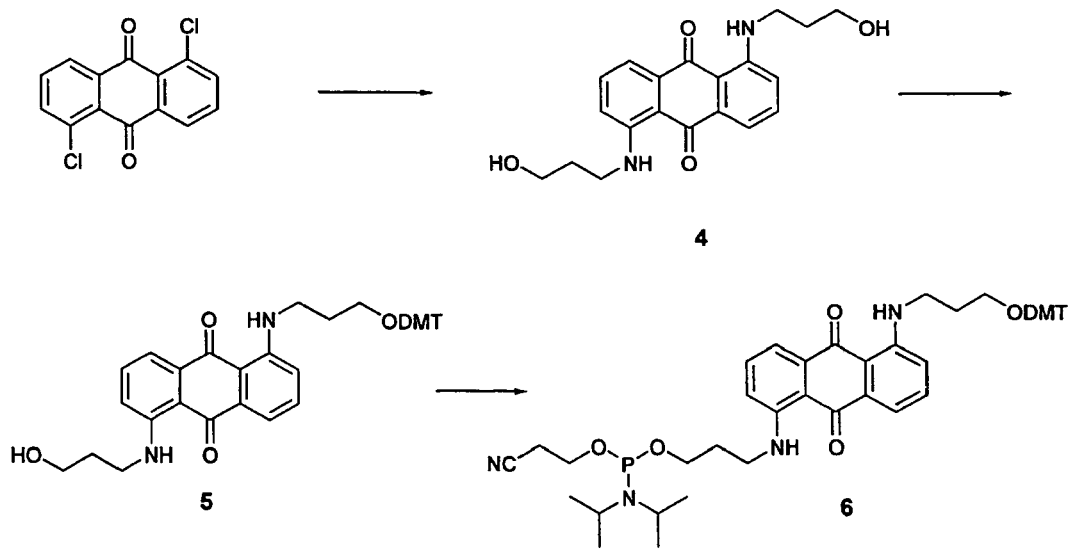
Figure 3:
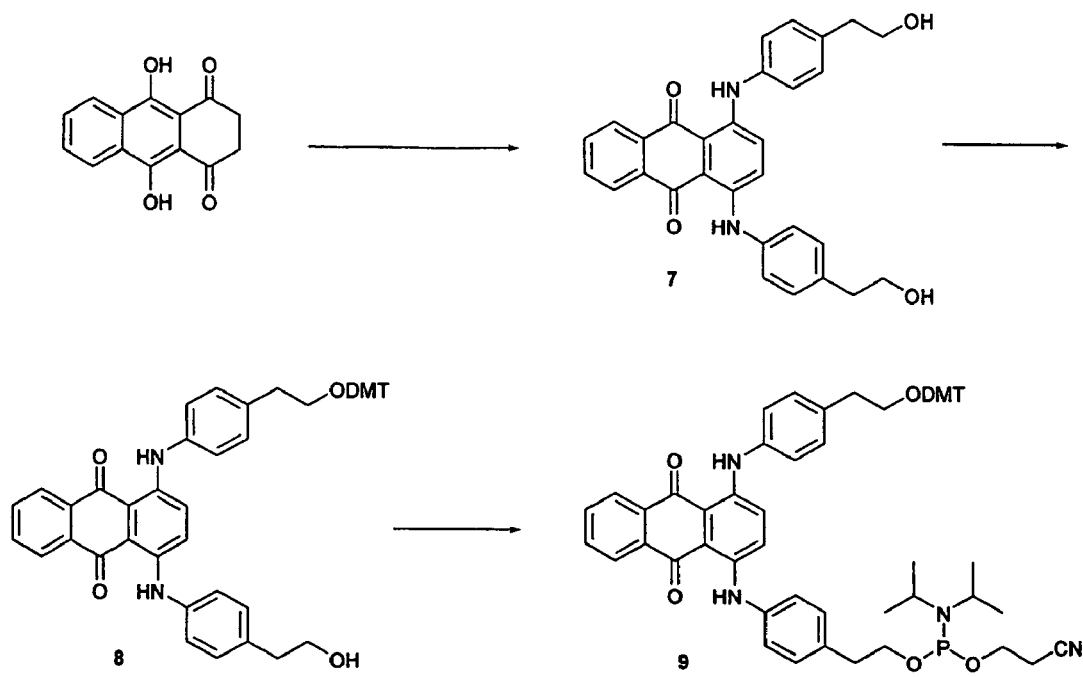
Figure 4:
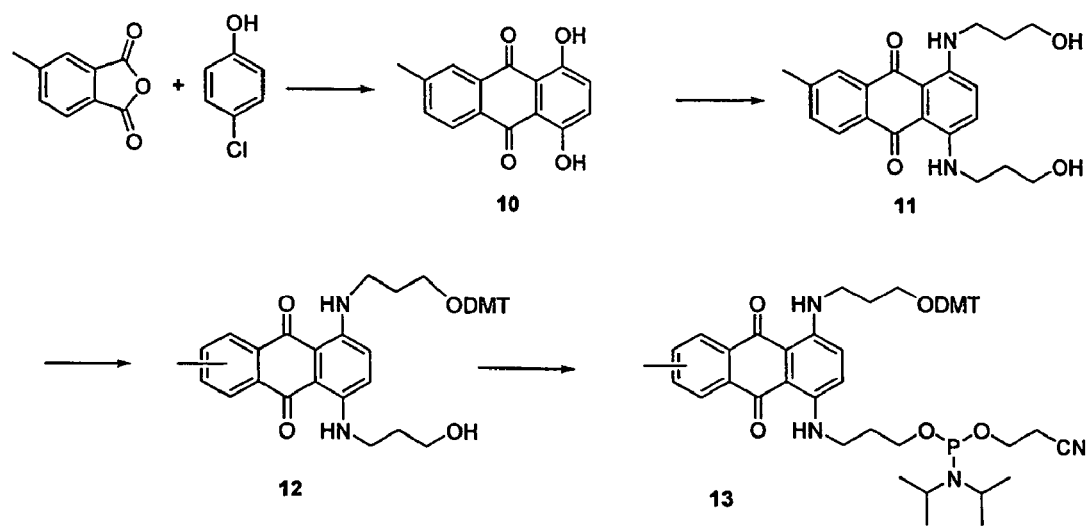
Figure 5:
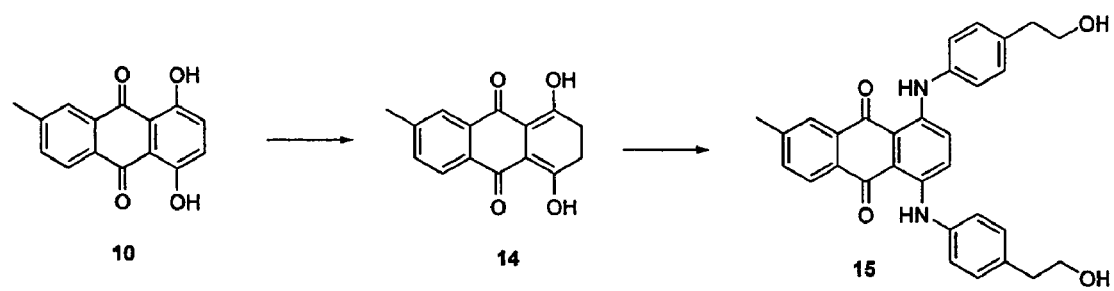
Figure 6:
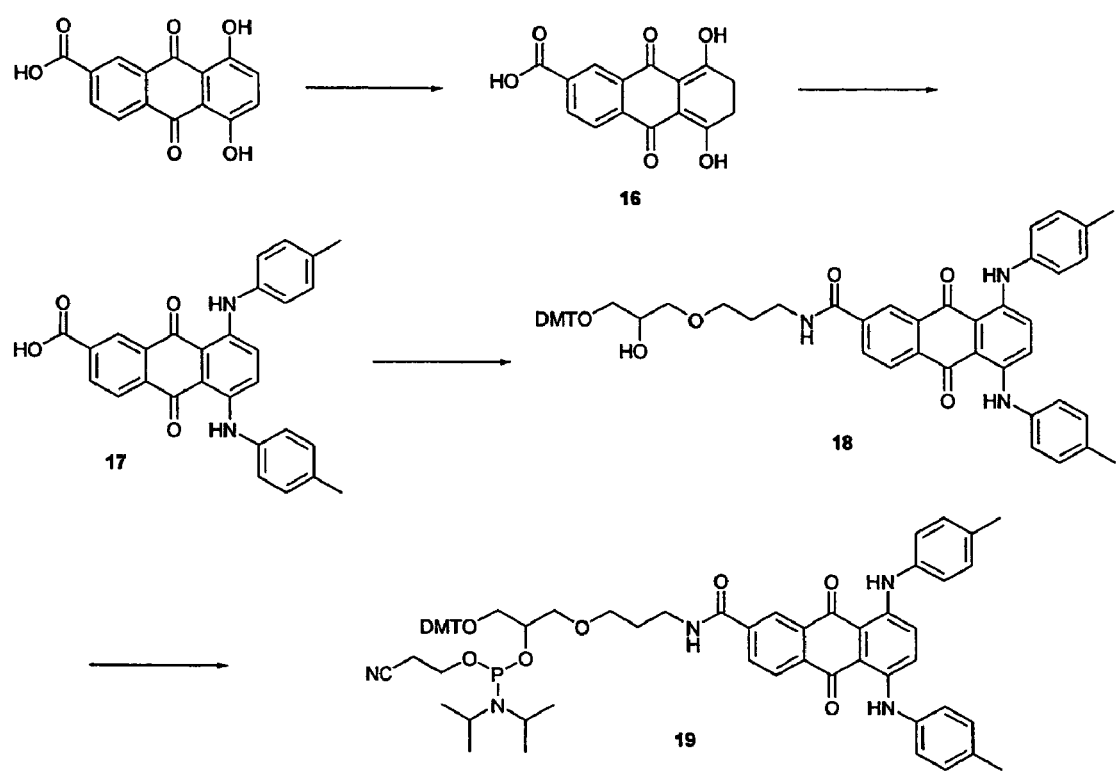
Figure 7:
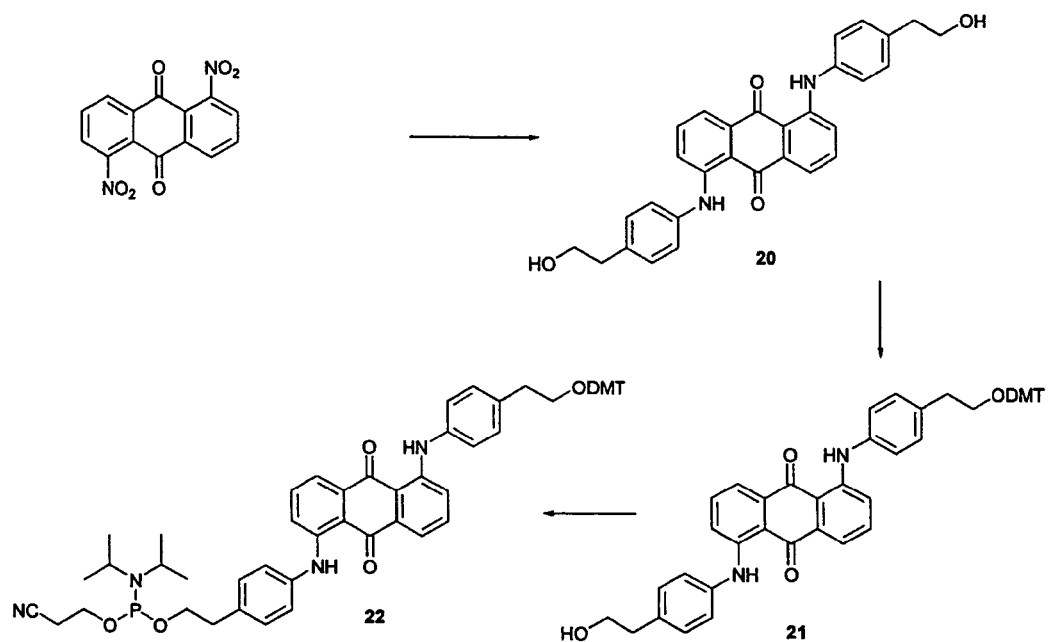
Figure 8:
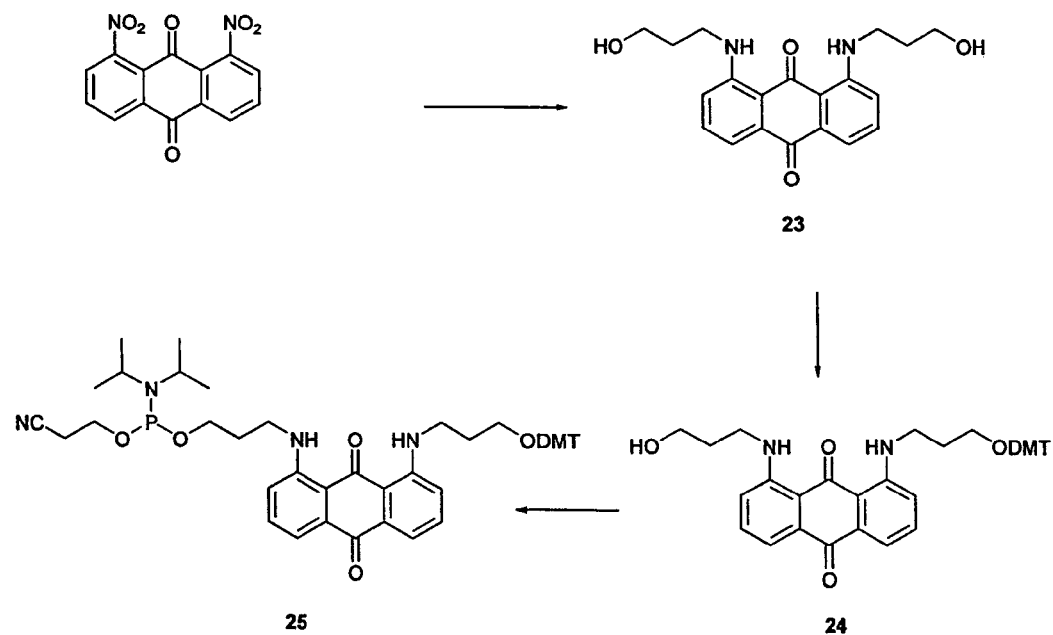
Figure 9:
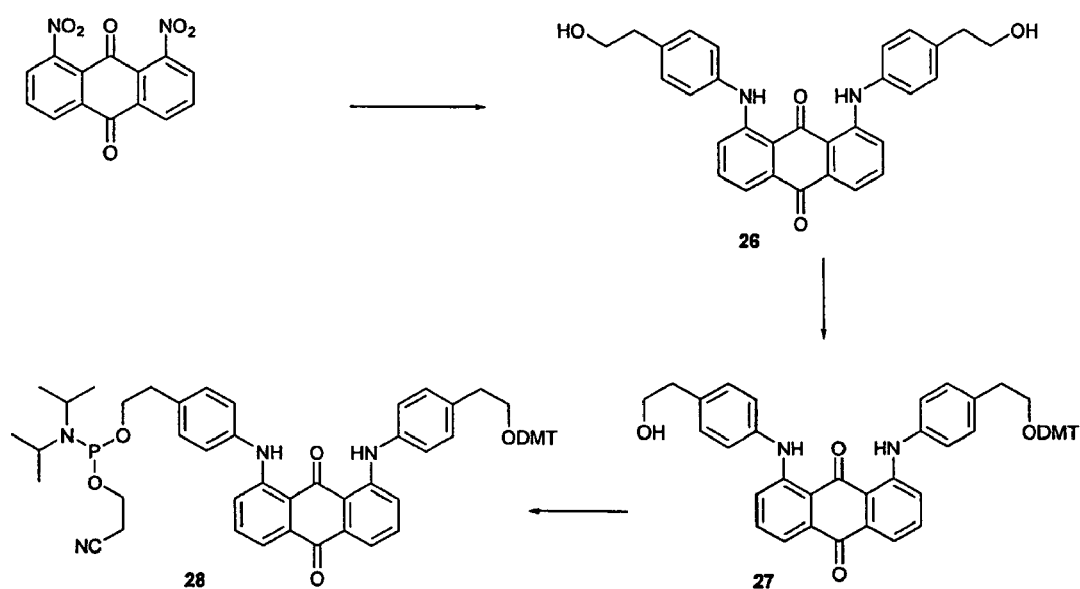

The present invention relates to a quencher composition of the formula (II):

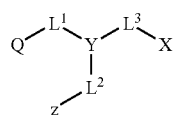

wherein Y is nitrogen or

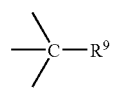

wherein $R^9$ is hydrogen, $C_1$-$C_6$-alkyl, or aryl;

$L^1$, $L^2$ and $L^3$ are each, independently, a bond or a linker;

X is a biomolecule or a protected form thereof, or an acid-labile or base-labile protecting group;

wherein the biomolecule is selected from an amino acid, a polypeptide, a nucleoside, a nucleotide, and a polynucleotide, and optionally further comprises a fluorophore;

Z is a bond or selected from —H, —$CO_2H$, —OH, —$NH_2$, —$NHR^{10}$, —$N(R^{10})_2$, —SH, a phosphate, a nucleotide, a substituted nucleotide, a polynucleotide, a substituted polynucleotide, an ester, a cleavable linker, a solid support, a reactive linking group, and a label;

all of which are optionally substituted with a label or a solid support;

and wherein $R^{10}$ is selected from $C_1$-$C_6$ alkyl, and aryl,

Q is a compound of the formula (I)

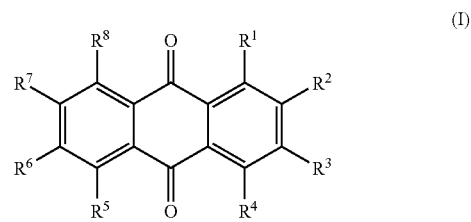

wherein at least one, two, three or four of $R^1$, $R^4$, $R^5$ or $R^8$ are each, independently selected from substituted or non-substituted amino-alkyl, amino-aryl and amino-alkylaryl, and the remaining $R^1$ to $R^8$ groups are each, independently hydrogen or substituted or non-substituted hydroxy, amino, alkyl, aryl, arylalkyl or alkoxy;

and wherein Q is attached to the linker $L^1$ either through one of the α-amino groups or through one of the aryl carbons of the quencher moiety.

The invention also relates to a quencher composition of the formula (III):

wherein $L^1$ and $L^2$ are each, independently a bond or a linker;

X is a biomolecule or a protected form thereof, or an acid-labile or base labile protecting group;

wherein the biomolecule is selected from an amino acid, a polypeptide, a nucleoside, a nucleotide and a polynucleotide, and optionally further comprises a fluorophore;

Z is a bond or selected from —H, —$CO_2H$, —OH, —$NH_2$, —$NHR^{10}$, —$N(R^{10})_2$, —SH, a phosphate, a nucleotide, a substituted nucleotide, a polynucleotide, a substituted polynucleotide, an ester, a cleavable linker, a solid support, a reactive linking group, and a label;

all of which are optionally substituted with a label or a solid support;

and wherein $R^{10}$ is selected from $C_1$-$C_6$ alkyl, and aryl,

Q is a compound of the formula (I)

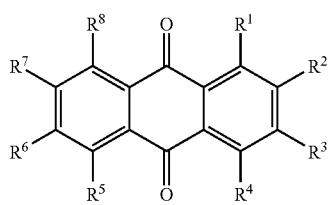

(I)

wherein at least one, two, three or four of $R^1$, $R^4$, $R^5$ or $R^8$ are each, independently selected from substituted or non-substituted amino-alkyl, amino-aryl and amino-alkylaryl, and the remaining $R^1$ to $R^8$ groups are each, independently hydrogen or substituted or non-substituted hydroxy, amino, alkyl, aryl, arylalkyl or alkoxy; and wherein Q is attached to the linkers $L^1$ and $L^2$ at two different positions, either through one of the α-aminogroups or through the aryl carbons of the quencher moiety.

In view of the publications of WO 2004/026804 A1, quencher compositions represented by the whole content of European patent application No. 20030759288 are preferably explicitly disclaimed from the quencher compositions of the formulae (II) and (III).

In the quencher compositions of the formula (II), $L^1$, $L^2$ and $L^3$ are preferably each, independently selected from $C_1$-$C_{12}$-alkyldiyl, $C_1$-$C_{12}$-alkoxydiyl, alkylaryl, $C_1$-$C_{12}$-alkylaminodiyl, $C_1$-$C_{12}$-alkylamidediyl, aryldiyl and 1-20 ethyleneoxy units.

In the quencher composition of the formula (III), $L^1$ and $L^2$ are preferably each, independently a bond or a linker, said linker being selected from alkylaryl, $C_1$-$C_{12}$-alkyldiyl, $C_1$-$C_{12}$-alkoxydiyl, $C_1$-$C_{12}$-alkylaminodiyl, $C_1$-$C_{12}$-alkylamidediyl, aryldiyl and 1-20 ethyleneoxy units.

In preferred embodiments, the group X in the quencher compositions of the formulae (II) and (III) is a biomolecule comprising a fluorophore and Z is a nucleotide or a polynucleotide both of which are optionally substituted with a label or a solid support.

In other embodiments, e.g. where the quencher compositions of the formulae (II) and (III) are prepared for further extension with nucleotides and polynucleotides, X is an acid labile protecting group and Z is a reactive linking group of the formula (IV):

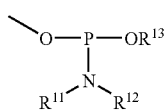

(IV)

wherein $R^{11}$ and $R^{12}$ are individually selected from isopropyl, methyl, ethyl, and $C_5$-$C_{14}$ aryl, or $R^{11}$ and $R^{12}$ are, when taken together, $C_4$-$C_{11}$ cycloalkyl or morpholine; and $R^{13}$ is $C_1$-$C_6$ alkyl, substituted $C_1$-$C_6$ alkyl, $C_5$-$C_{14}$ aryl or a protecting group; in particular $R^{11}$ and $R^{12}$ are both isopropyl and $R^{13}$ is cyanoethyl. X as the protecting group is typically selected from the group consisting of DMT, MMT, trityl, substituted trityl, pixyl and trialkylsilyl.

In still further embodiments, the quencher composition is immobilized on a solid support in a manner so that the quencher composition can be cleaved from said solid support. In such embodiments, Z may have a structure of the formula (V):

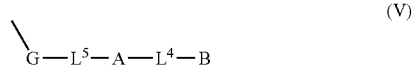

(V)

wherein A is a cleavable linker selected from the structures (Va-Vf):

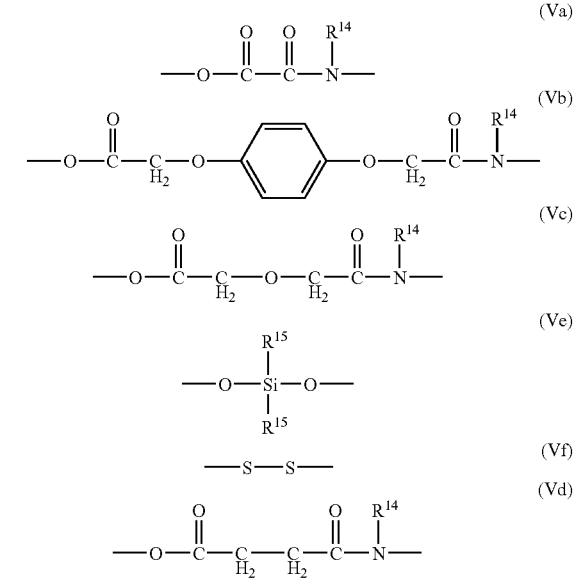

wherein $R^{14}$ is $C_{1-12}$ alkyl or $C_{1-12}$ alkoxy; $R^{15}$ is alkyl, aryl, arylalkyl or alkoxy; $L^4$ and $L^5$ are independently selected from a bond and a linker, said linker being selected from $C_1$-$C_{12}$-alkyldiyl, $C_1$-$C_{12}$-alkoxydiyl, $C_1$-$C_{12}$-alkylaminodiyl, $C_1$-$C_{12}$-alkylamidedlyl, aryldlyl and 1-20 ethyleneoxy units; G is a bond, a nucleotide, a substituted nucleotide, a polynucleotide, a substituted polynucleotide or a hybridization-stabilizing moiety; and B is a solid support.

In one variant of the above, G is a hybridization-stabilizing moiety, e.g. comprising the structure:

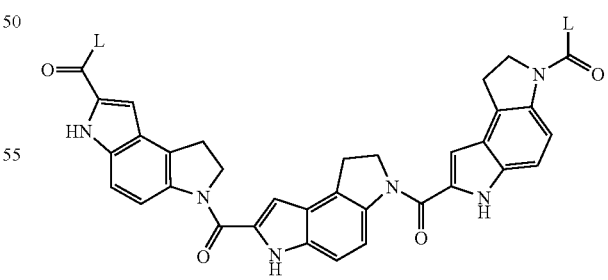

wherein L designates the sites of attachment to $L^2$ and $L^5$.

In the above embodiment, the solid support is typically selected from polystyrene, controlled-pore-glass (CPG), silica gel, silica, polyacrylamide, a magnetic material, polyacrylate, hydroxyethylmethacrylate, polyamide, polyethylene, and polyethyleneoxy, and copolymers and grafts of such.

The form of the solid support is typically selected from a particle, a bead (e.g. a magnetic bead), a membrane, a frit, a fiber, a tube, a capillary, a slide, a plate, a micromachined chip, an alkanethiol-gold layer, a non-porous surface, an addressable array, and polynucleotide-immobilizing medium.

In one important embodiment which is further described below and illustrated in the examples section, X is a polynucleotide comprising a fluorescent dye.

In some variants hereof, the polynucleotide comprises one or more N-[2-(aminoethyl)]-glycine units having a nucleobase attached to nitrogen through a methylene carbonyl linkage. Such units are normally known as units of a PNA molecule.

In other variants hereof, which are particularly preferred, the polynucleotide comprises one or more of 2'-4' or 3'-4' bicyclic sugar modifications. Such sugar modifications are normally known as LNA.

Particularly interesting variants of the quencher composition (III) are those wherein $L^1$ and $L^2$ are each, independently a bond or a linker; X is a polynucleotide comprising a fluorescent dye; Z is a nucleotide or a polynucleotide both of which are optionally substituted with a label or a solid support; and Q is as described above.

In a preferred embodiment of the invention, the α-amino substituted anthraquinone compounds of the formula (I) are di-α-amino substituted.

With respect to the particular quencher compound, Q, it is believed that those selected from 1,4-bis-(3-hydroxy-propylamino)-anthraquinone (1), 1-(3-(4,4'-dimethoxy-trityloxy)propyl-amino)-4-(3-hydroxypropylamino)-anthraquinone (2), 1,5-bis-(3-hydroxy-propylamino)-anthraquinone (4), 1-(3-hydroxypropylamino)-5-(3-(4,4'-dimethoxy-trityloxy)propylamino)-anthraquinone (5), 1,4-bis-(4-(2-hydroxy-ethyl)phenylamino)-anthraquinone (7), 1-(4-(2-(4,4'-dimethoxy-trityloxy)ethyl)phenylamino)-4-(4-(2-hydroethyl)phenylamino)-anthraquinone (8), and 1,8-bis-(3-hydroxy-propylamino)-anthraquinone, are particularly useful for the quencher compositions of the formula (II), and that those selected from 1,4-bis-(3-hydroxy-propylamino)-anthraquinone (1), 1,5-bis-(3-hydroxy-propylamino)-anthraquinone (4), 1,4-bis-(4-(2-hydroxyethyl)phenylamino)-anthraquinone (7), and 1,8-bis-(3-hydroxy-propylamino)-anthraquinone, are particularly useful for the quencher compositions of the formula (III).

As alternatives, quencher compounds, Q, selected from 1,4-bis(3-hydroxypropylamino)-6-methylanthraquinone (11), 1-(3-(4,4'-dimethoxy-trityloxy)propylamino)-4-(3-hydroxy-propylamino)-6(7)-methyl-anthraquinone (12), 1,4-bis(4-(2-hydroethyl)phenylamino)-6-methyl-anthraquinone (15), 1,4-bis(4-methyl-phenylamino)-6-carboxy-anthraquinone (17), 1,4-bis(4-methyl-phenylamino)-6-(N-(6,7-dihydroxy-4-oxo-heptane-1-yl))carboxamido-anthraquinone, 1,4-bis(4-methyl-phenylamino)-6-(N-(7-dimethoxytrityloxy-6-hydroxy-4-oxo-heptane-1-yl))carboxamido-anthraquinone (18), 1,4-bis(propylamino)-6-carboxy-anthraquinone, 1,4-bis(propylamino)-6-(N-(6,7-dihydroxy-4-oxo-heptane-1-yl))carboxamido-anthraquinone, 1,4-bis(propylamino)-6-(N-(7-dimethoxytrityloxy-6-hydroxy-4-oxo-heptane-1-yl))carboxamido-anthraquinone, 1,5-bis(4-(2-hydroethyl)phenylamino)-anthraquinone (20), 1-(4-(2-hydroethyl)phenylamino)-5-(4-(2-(4,4'-dimethoxytrityloxy)ethyl)phenylamino)-anthraquinone (21), 1,8-bis(3-hydroxypropylamino)-anthraquinone (23), 1-(3-hydroxypropylamino)-8-(3-(4,4'-dimethoxytrityloxy)propylamino)-anthraquinone (24), 1,8-bis(4-(2-hydroethyl)phenylamino)-anthraquinone (26), and 1-(4-(2-hydroethyl)phenylamino)-8-(4-(2-(4,4'-dimethoxytrityloxy)ethyl)phenylamino)-anthraquinone (27), are believed to be useful for the quencher compositions of the formula (II), and quencher compounds, Q, selected from 1,4-bis(3-hydroxypropylamino)-6-methylanthraquinone (11), 1,4-bis(4-(2-hydroethyl)phenylamino)-6-methyl-anthraquinone (15), 1,4-bis(4-methyl-phenylamino)-6-(N-(6,7-dihydroxy-4-oxo-heptane-1-yl))carboxamido-anthraquinone, 1,4-bis(4-methyl-phenylamino)-6-(N-(7-dimethoxytrityloxy-6-hydroxy-4-oxo-heptane-1-yl))carboxamido-anthraquinone (118), 1,4-bis(propylamino)-6-(N-(6,7-dihydroxy-4-oxo-heptane-1-yl))carboxamido-anthraquinone, 1,5-bis(4-(2-hydroethyl)phenylamino)-anthraquinone (20), 1-(4-(2-hydroethyl)phenylamino)-5-(4-(2-(4,4'-dimethoxy-trityloxy)ethyl)phenylamino)-anthraquinone (21), 1,8-bis(3-hydroxypropylamino)-anthraquinone (23), 1-(3-hydroxypropylamino)-8-(3-(4,4'-dimethoxytrityloxy)propylamino)-anthraquinone (24), 1,8-bis(4-(2-hydroethyl)phenylamino)-anthraquinone (26), and 1-(4-(2-hydroethyl)phenylamino)-8-(4-(2-(4,4'-dimethoxytrityloxy)ethyl)phenylamino)-anthraquinone (27), are believed to be useful for quencher compositions of the formula (III).

It should be understood that although the quencher compounds, Q, are mentioned as the discrete molecules, Q is attached to the linker(s) $L^1$ (and $L^2$) at one or two different positions, either through one of the β-amino groups or through the aryl carbons of the quencher moiety. Preferably, however, Q is attached to the linker(s) $L^1$ (and $L^2$) via the O-atom of the hydroxy groups.

It is believed that some of the quencher compounds are novel as such, thus, it should be understood that the present invention also relates to quencher compounds selected from 1,4-bis-(3-hydroxy-propylamino)-anthraquinone (1), 1-(3-(4,4'-dimethoxy-trityloxy)propylamino)-4-(3-hydroxypropylamino)-anthraquinone (2), 1-(3-(2-cyanoethoxy(diisopropylamino)phosphinoxy)propylamino)-4-(3-(4,4'-dimethoxy-trityloxy)propylamino)-anthraquinone (3), 1,5-bis-(3-hydroxy-propylamino)-anthraquinone (4), 1-(3-hydroxypropylamino)-5-(3-(4,4'-dimethoxy-trityloxy)propylamino)-anthraquinone (5), 1-(3-(cyanoethoxy(diisopropylamino)phosphinoxy)propylamino)-5-(3-(4,4'-dimethoxy-trityloxy)propylamino)-anthraquinone (6), 1,4-bis-(4-(2-hydroxyethyl)phenylamino)-anthraquinone (7), 1-(4-(2-(4,4'-dimethoxy-trityloxy)ethyl)phenylamino)-4-(4-(2-hydroethyl)phenylamino)-anthraquinone (8), 1-(4-(2-(2-cyanoethoxy(diisopropylamino)-phosphinoxy)ethyl)phenylamino)-4-(4-(2-(4,4'-dimethoxy-trityloxy)ethyl)phenylamino)-anthraquinone (9), and 1,8-bis-(3-hydroxy-propylamino)-anthraquinone; or alternatively selected from 6-methyl-Quinizarin (10), 1,4-bis(3-hydroxypropylamino)-6-methylanthraquinone (11), 1-(3-(4,4'-dimethoxy-trityloxy)propylamino)-4-(3-hydroxypropylamino)-6(7)-methyl-anthraquinone (12), 1-(3-(2-cyanoethoxy(diisopropylamino)-phosphinoxy)propylamino)-4-(3-(4,4'-dimethoxy-trityloxy)propylamino)-6(7)-methylanthraquinone (13), 1,4-bis(4-(2-hydroethyl)phenylamino)-6-methyl-anthraquinone (15), 1,4-Dihydroxy-2,3-dihydro-6-carboxy-anthraquinone (16), 1,4-bis(4-methyl-phenylamino)-6-carboxy-anthraquinone (17), 1,4-bis(4-methyl-phenylamino)-6-(N-(6,7-dihydroxy-4-oxo-heptane-1-yl))carboxamido-anthraquinone, 1,4-bis(4-methyl-phenylamino)-6-(N-(7-dimethoxytrityloxy-6-hydroxy-4-oxo-heptane-1-yl))carboxamido-anthraquinone (18), 1,4-Bis(4-methyl-phenylamino)-6-(N-(7-(2-cyanoethoxy(diisopropylamino)phosphinoxy)-6-hydroxy-4-oxo-heptane-1-yl))carboxamido-anthraquinone (19), 1,4-bis(propylamino)-6-carboxy-anthraquinone, 1,4-bis(propylamino)-6-(N-(6,7-dihydroxy-4-oxo-heptane-1-yl))carboxamido-anthraquinone, 1,4-bis(propylamino)-6-(N-(7-dimethoxytrityloxy-6-hydroxy-4-oxo-heptane-1-yl)) carboxamido-anthraquinone, 1,5-bis(4-(2-hydroethyl)-phenylamino)-anthraquinone (20), 1-(4-(2-hydroethyl) phenylamino)-5-(4-(2-(4,4'-dimethoxy-trityloxy)ethyl) phenylamino)-anthraquinone (21), 1-(4-(2-(cyanoethoxy-(diisopropylamino)phosphinoxy)ethyl)phenylamino)-5-(4-(2-(4,4'-dimethoxy-trityloxy)ethyl)phenylamino)-anthraquinone (22), 1,8-bis(3-hydroxypropylamino)-anthraquinone (23), 1-(3-hydroxypropylamino)-8-(3-(4,4'-dimethoxy-trityloxy)-propylamino)-anthraquinone (24), 1,8-bis(4-(2-hydroethyl)phenylamino)-anthraquinone (26), and 1-(4-(2-hydroethyl)phenylamino)-8-(4-(2-(4,4'-dimethoxy-trityloxy)ethyl)phenylamino)-anthraquinone (27).

Another aspect of the present invention relates to a polynucleotide probe containing at least one quencher composition as described above. In addition to the quencher moiety, the probe preferably further comprises at least one quenchable label. Typically, the quenchable label is separated from the quencher by a nuclease susceptible site. In this case, the polynucleotide probe is typically blocked for extension by the polymerase in the 3'end.

The probe described above, can typically adopt at least 1 conformation when not bound to the target where the label is quenched by the quencher, and at least one other conformation when the probe is bound to the target where the label is at least partially unquenched by the quencher. In one variant, a 3' part and a 5' part of the polynucleotide are perfectly complementary such as to form a hairpin structure when not bound to the target.

More generally, it is preferred that the polynucleotide probe comprises at least one target recognition region complementary to a target gene.

The polynucleotide probe, including the variants described above, typically has a length of 5 to 50 nucleotides.

A further aspect of the invention relates to a method of primer extension comprising: annealing a polynucleotide primer to a target polynucleotide; and extending the primer by polymerase-mediated incorporation of a nucleotide 5'-triphosphate; wherein the primer or the nucleotide 5'-triphosphate is attached to a quencher moiety of the formula (I) (preferably as defined as for quencher composition (II) and (III)); whereby a labelled polynucleotide is formed. Typically, the method further comprises the step of amplifying the target polynucleotide with nucleotide 5'-triphosphates, a polymerase, and two or more primers (typically by the polymerase chain reaction, or another nucleic acid amplification method); wherein the primers are complementary to the target polynucleotide sequence and at least one primer is attached to a quencher moiety of the formula (I).

A still further aspect of the invention relates to a method of amplifying a target polynucleotide comprising nucleotide 5'-triphosphates, a polymerase, two or more primers; wherein the primers are complementary to the target polynucleotide sequence, and a detectably labelled probe; wherein at least a part of the detectably labelled probe is complementary to the target polynucleotide and comprises at least a fluorescent dye and a quencher moiety of the formula (I) (preferably as defined as for quencher composition (II) and (III)). Preferably, the method further comprises detecting a signal from the fluorescent dye of said detectable probe. Typically, the signal is detected at each thermal cycle during amplification.

In a further variant of the method, the polymerase cleaves the detectable probe during amplification; whereby the fluorescent dye and the quencher moiety are separated. Like before, the method preferably further comprises detecting a signal from the fluorescent dye of said cleaved, detectable probe. Typically, the signal is detected at each thermal cycle during amplification.

Hybridization to the target polynucleotide may be monitored by FRET and used to detect the target sequence. The probe may be cleaved by nuclease activity of an enzyme during nucleic acid amplification. Cleavage may generate a detectable signal and used to monitor and detect nucleic acid hybridization and amplification. The primers and probes may be further labeled with hybridization-stabilizing moieties, such as minor groove binders.

In a still further variant of the method, the fluorescent dye is attached to the 5' terminus or 3' terminus of the detectable probe. Still further, the quencher moiety is attached to the 5' terminus or 3' terminus of or internally in the detectable probe.

In a particular variant of the method, the detectable probe is further labelled with a hybridization-stabilizing moiety, e.g. a hybridization-stabilizing moiety comprising the structure:

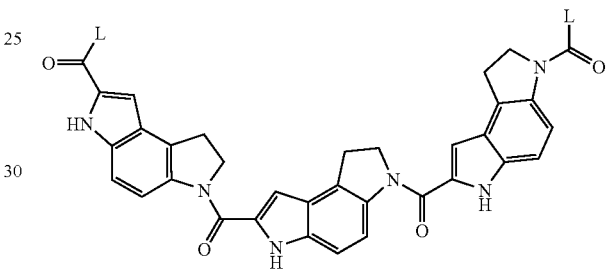

where L is an attachment site to the detectable probe.

In other variants of the method, the detectable probe has a format selected from molecular beacons, scorpion probes, sunrise probes, conformationally assisted probes and TaqMan probes.

In still other variants of the method, the detectable probe comprises one or more one or more N-[2-(aminoethyl)]glycine units having a nucleobase attached to nitrogen through a methylene carbonyl linkage, or the detectable probe comprises one or more of 2'-4' or 3'-4' bicyclic sugar modifications.

A still further aspect of the invention relates to a method of hybridization detection comprising annealing a probe to a target polynucleotide sequence, wherein the probe is covalently attached to a fluorescent dye and a quencher moiety of the formula (I) (preferably as defined as for quencher composition (II) and (III)); and detecting a signal from the fluorescent dye.

The invention further includes kits or reagents for performing the methods and uses detailed herein. The kits may contain the fluorescence quencher compositions, biomolecules labeled with the quencher moieties, and/or other reagents.

A still further aspect of the invention relates to a kit for nucleic acid amplification comprising two or more primers, and a probe with a detectable label and a quencher moiety of the formula (I) (preferably as defined as for quencher composition (II) and (III)).

Another aspect of the invention relates to a kit for primer extension comprising one or more nucleotide 5'-triphosphates and one or more primers wherein at least one primer is covalently attached by a linkage to an aryl carbon of a quencher moiety of the formula (I) (preferably as defined as for quencher composition (II) and (III)).

A further aspect of the Invention relates to a microarray comprising a quencher moiety of the formula (I) (preferably as defined as for quencher composition (II) and (III)), said quencher being conjugated directly to a solid support or to a carrier molecule attached to said solid support.

A still further aspect of the invention relates to a method of probing a microarray for the presence of a compound, said method comprising: (a) contacting said microarray with a probe interacting with said compound, said probe comprising a quencher moiety of the formula (I) (preferably as defined as for quencher composition (II) and (III)); (b) detecting a difference in a fluorescence property of a member selected from said probe, said compound and combinations thereof, thereby ascertaining the presence of said compound.

A even further aspect of the invention relates to detection systems, for example (A) a detection system comprising: (a) a target binding entity, (b) a quenchable detectable label and (c) a quencher composition of the formulae (II) or (III), wherein the quenchable label and the quencher each are positioned on the target binding entity and/or the target such that the label is quenched by the quencher when the target binding entity is unbound to its target, and such that binding of the binding entity to its target will remove the quencher from the label such that the label is at least partially unquenched; and (B) a detection system comprising: (a) a target binding entity, (b) a quenchable detectable label and (c) a quencher composition of the formulae (II) or (III), wherein the quenchable label and the quencher each are positioned on the target binding entity and/or the target such that the label is at least partially unquenched by the quencher when the target binding entity is unbound to its target, and such that binding of the binding entity to its target will bring the quencher in vicinity of the label such that the label is at least partially quenched.

In such detection systems, the target binding entity preferably comprises a polynucleotide, an antibody, an aptamer, or a ligand.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING : A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

In the above structural formulae and throughout the present specification, the following terms have the indicated meaning:

The term "alkyl" is used herein to refer to a branched or unbranched, saturated or unsaturated, monovalent hydrocarbon radical, generally having from about 1-30 carbons and preferably, from 1-6 carbons. Suitable alkyl radicals include, for example, structures containing one or more methylene, methine and/or methyne groups. Branched structures have a branching motif similar to iso-propyl, t-butyl, i-butyl, 2-ethylpropyl, etc. As used herein, the term encompasses "substituted alkyls" and "cyclic alkyl". "Substituted alkyl" refers to alkyl as just described including one or more substituents such as, for example, $C_1$-$C_6$-alkyl, aryl, acyl, halogen (i.e. alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "alkylaryl" means a radical obtained by combining an alkyl and an aryl group. Typical alkylaryl groups include phenethyl, ethyl phenyl and the like.

The term "amino-alkyl" means amino substituted with alkyl. In a preferred embodiment, the amino group is attached to the anthraquinone structure.

The term "amino-alkylaryl" means amino substituted with alkylaryl. In a preferred embodiment, the amino group is attached to the anthraquinone structure.

The term "amino-aryl" means amino substituted with aryl. In a preferred embodiment, the amino group is attached to the anthraquinone structure.

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "aryl" means a monovalent aromatic hydrocarbon radical of 5-14 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like, including substituted aryl groups. "Substituted aryl" refers to aryl as just described including one or more substituents such as, for example, $C_1$-$C_6$-alkyl, aryl, acyl, halogen (i.e. alkylhalos, e.g., $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the aryl moiety.

The term "aryldiyl" means an unsaturated cyclic or polycyclic hydrocarbon radical of 5-14 carbon atoms having a conjugated resonance electron system and at least two monovalent radical centers derived by the removal of two hydrogen atoms from two different carbon atoms of a parent aryl compound, including substituted aryldiyl groups.

The term "biomolecule" encompasses an amino acid, a polypeptide, a nucleoside, a nucleotide, a polynucleotide, a carbohydrate, a vitamin, a hormone, and any other compound produced by an organism.

The term "alkoxydiyl" as in "$C_1$-$C_{12}$-alkoxydiyl" means an alkoxyl group having two monovalent radical centers derived by the removal of a hydrogen atom from the oxygen and a second radical derived by the removal of a hydrogen atom from a carbon atom. Typical alkoxydiyl radicals include, but are not limited to, methoxydiyl (—$OCH_2$—) and 1,2-ethoxydiyl or ethyleneoxy (—$OCH_2CH_2$—).

The term "alkylamidediyl" as in "$C_1$-$C_{12}$-alkylamidediyl" means an alkylamide group having two monovalent radical centers derived by the removal of a hydrogen atom from the nitrogen and a second radical derived by the removal of a hydrogen atom from a carbon atom. Typical alkylamidediyl radicals include, but are not limited to —NHC(O)CH$_2$—, —NHC(O)CH$_2$CH$_2$—, and —NHC(O)CH$_2$CH$_2$CH$_2$—.

The term "alkylaminodiyl" as in "$C_1$-$C_{12}$-alkylaminodiyl" means an alkylamino group having two monovalent radical centers derived by the removal of a hydrogen atom from the nitrogen and a second radical derived by the removal of a hydrogen atom from a carbon atom. Typical alkylaminodiyl radicals include, but are not limited to —NHCH$_2$—, —NHCH$_2$CH$_2$—, and —NHCH$_2$CH$_2$CH$_2$—.

The term "alkyldiyl" as in "$C_1$-$C_{12}$-alkyldiyl" means a saturated or unsaturated, branched, straight chain, cyclic, or substituted hydrocarbon radical of 1-12 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl (—CH$_2$CH$_2$—), 1,3-propyldiyl(—CH$_2$CH$_2$CH$_2$—), 1,4-butyldiyl(—CH$_2$CH$_2$CH$_2$CH$_2$—), and the like.

The term "cleavable linker" is a linker which has one or more covalent bonds which may be broken by the result of a reaction or condition. For example, an ester in a molecule is a linker that may be cleaved by a reagent, e.g. sodium hydroxide, resulting in a carboxylate-containing fragment and a hydroxyl-containing product.

The term "end-point analysis" refers to a method where data collection occurs only when a reaction is substantially complete.

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labelling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28). Fluorescent reporter dyes useful for labelling biomolecules include fluoresceins (U.S. Pat. Nos. 5,188,934; 6,008,379; 6,020,481), rhodamines (U.S. Pat. Nos. 5,366,860; 5,847, 162; 5,936,087; 6,051,719; 6,191,278), benzophenoxazines (U.S. Pat. No. 6,140,500), energy-transfer dye pairs of donors and acceptors (U.S. Pat. Nos. 5,863,727; 5,800,996; 5,945, 526), and cyanines (Kubista, WO 97/45539), as well as any other fluorescent label capable of generating a detectable signal. Examples of fluorescein dyes include 6-carboxyfluorescein; 2',4',1,4,-tetrachlorofluorescein; and 2',4',5',7',1,4-hexachlorofluorescein. See Example 50 and Menchen, U.S. Pat. No. 5,118,934. Another class of labels are hybridization-stabilizing moieties which serve to enhance, stabilize, or influence hybridization of duplexes, e.g. interchalators, minor-groove binders, and cross-linking functional groups (Blackburn, G. and Gait, M. Eds. "DNA and RNA structure" in Nucleic Acids in Chemistry and Biology, 2Edition, (1996) Oxford University Press, pp. 15-81). Yet another class of labels ("affinity ligands") effect the separation or immobilization of a molecule by specific or non-specific capture, for example biotin, digoxigenin, and other haptens (Andrus, A. "Chemical methods for 5' non-isotopic labelling of PCR probes and primers" (1995) in PCR 2: A Practical Approach, Oxford University Press, Oxford, pp. 39-54). Non-radioactive labelling methods, techniques, and reagents are reviewed in: Non-Radioactive Labelling, A Practical Introduction, Garman, A. J. (1997) Academic Press, San Diego.

The term "nucleobase" means any nitrogen-containing heterocyclic moiety capable of forming Watson-Crick hydrogen bonds in pairing with a complementary nucleobase or nucleobase analogue, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebuiarine, nitropyrrole, nitroindole, 2-amino-purine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, O-methylguanine, N-methyl-adenine, O-methylthymine, 5,6-dihydrothymine, 5,6-dihydrouracil, 4-methylindole, pyrazolo[3,4-D]pyrimidines (U.S. Pat. Nos. 6,143,877 and 6,127,121; WO 01/38584), and ethenoadenine (Fasman (1989) in Practical Handbook of Biochemistry and Molecular Biology, pp. 385-394, CRC Press, Boca Raton, Fla.).

The term "nucleoside" refers to a compound consisting of a nucleobase linked to the C-1' carbon of a sugar, such as ribose, arabinose, xylose, and pyranose. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$-alkyl or $C_5$-$C_{14}$-aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-[alpha]-anomeric nucleotides, 1'-[alpha]-anomeric nucleotides, 2'-4'- and 3'-4'-linked and other "locked" or "LNA", bicyclic sugar modifications (WO 98/22489; WO 98/39352; WO 99/14226). Modifications at the 2'- or 3'-position of ribose include hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D optical isomer, as well as the L optical isomer forms (Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleobase is purine, e.g. A or G, the ribose sugar is attached to the N-position of the nucleobase. When the nucleobase is pyrimidine, e.g. C, T or U, the pentose sugar is attached to the N-position of the nucleobase (Komberg and Baker, (1992) DNA Replication, 2Ed., Freeman, San Francisco, Calif.).

The term "nucleotide" refers to a phosphate ester of a nucleoside, as a monomer unit or within a nucleic acid. "Nucleotide 5"-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. [alpha]-thio-nucleotide 5'-triphosphates. For a review of nucleic acid chemistry, see: Shabarova, Z. and Bogdanov, A. Advanced Organic Chemistry of Nucleic Acids, VCH, New York, 1994.

As used herein, the terms "polynucleotide" and "oligonucleotide" are used interchangeably and mean singlestranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H, $NH_4^+$, trialkylammonium, $Mg^{+2}$, $Na^+$ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted. The polynucleotides or oligonucleotides are not restricted to naturally occurring nucleotide and may comprise one or more nucleotide analogues in the sequence. The polynucleotides can be substituted as disclosed in "Current Protocols in Nucleic Acid Chemistry", edit by S. L. Beaucage et. al., John Wiley Sons, Inc. 1999, Chapter 4.

The term "polypeptide" refers to a polymer including proteins, synthetic peptides, antibodies, peptide analogs, and peptidomimetics in which the monomers are amino acids and are joined together through amide bonds. When the amino acids are [alpha]-amino acids, either the L-optical isomer or the D-optical isomer can be used. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in Chemistry and Biochemistry of Amino Acids, Peptides and Proteins, B. Weinstein, eds., Marcel Dekker, New York, p. 267 (1983). The term "amino acid" refers to naturally occurring and synthetic amino acids, as well as amino acid analogs and amino acid mimetics that function in a manner choices can be found in many art recognized references.

The expression "enzymatically extendable" in connection with "primer extension" refers to a nucleotide which is: (i) capable of being enzymatically incorporated onto the terminus of a polynucleotide chain through the action of a polymerase enzyme, and (ii) capable of supporting further primer extension. Enzymatically extendable nucleotides include nucleotide 5'-triphosphates, i.e. dNTP and NTP.

The term "probe" means a polynucleotide that is capable of forming a duplex structure by complementary base pairing with a sequence of a target nucleic acid. For example, probes may be labelled, e.g. with a quencher moiety, or an energy transfer pair comprised of a fluorescent reporter and quencher.

A "protecting group" is a functionality that is removed either through a chemically or physically interaction whereby a new functional group is formed. An "acid labile protecting group" is a functionality that is removed when subjected to acidic conditions. Suitable acid labile protecting groups include trityl (triphenylmethyl), MMT (4-momomethoxytrityl), DMT (4,4'-dimethoxytrityl), substituted trityl and pixyl (9-phenyl-xanthene-9-yl). A "base labile protecting group" is a functionality that is removed when subjected to basic conditions. Suitable base labile protecting groups include acetyl, benzoyl, 2-cyanoethyl, 4-cyano-2-butenyl, 4-oxo-pentyl and 3-(N-tert-butylcarboxamido)-1-propyl. A "photo-cleavable protecting group" is a functionality that is removed when irradiated with light of a specific wavelength.

The term "quenching" refers to a decrease in fluorescence of a fluorescent reporter ran moiety caused by a quencher moiety by energy transfer, regardless of the mechanism. Hence, illumination of the fluorescent reporter in the presence of the quencher leads to an emission signal that is less intense than expected, or even completely absent.

The term "reactive linking group" refers to a chemically reactive substituent or moiety, e.g. a nucleophile or electrophile, on a molecule which is capable of reacting with another molecule to form a covalent bond. Reactive linking groups include active esters, which are commonly used for coupling with amine groups. For example, N-hydroxysuccinimide (NHS) esters have selectivity toward aliphatic amines to form aliphatic amide products which are very stable. Their reaction rate with aromatic amines, alcohols, phenols (tyrosine), and histidine is relatively low. Reaction of NHS esters with amines under nonaqueous conditions is facile, so they are useful for derivatization of small peptides and other low molecular weight biomolecules. Virtually any molecule that contains a carboxylic acid or that can be chemically modified to contain a carboxylic acid can be converted into its NHS ester. NHS esters are available with sulfonate groups that have improved water solubility. Reactive linking groups also include active phosphor compounds normally referred to as phosphoramidites as described in S. L. Beaucage and M. H. Caruthers, Chapter 3.3 in "Curent Protocols in Nucleic Acid Chemistry", edit by S. L. Beaucage et. al., John Wiley Sons, Inc. 1999.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "solid support" refers to any solid phase material upon which a nucleic acid or polypeptide is synthesized, attached or immobilized. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, or a surface. Surfaces may be planar, substantially planar, or non-planar. Solid supports may be porous or non-porous, and may have swelling or non-swelling characteristics. A solid support may be configured in the form of a well, depression or other vessel. A plurality of solid supports may be configured in an array, addressable for robotic delivery of reagents, or by detection means including scanning by laser illumination and confocal or deflective light gathering.

EXAMPLES

Processes for preparing compounds for use in the novel quencher compositions are further illustrated in the following examples, which however, are not to be construed as limiting. The structures of the compounds are confirmed by either elemental analysis (MA) nuclear magnetic resonance (NMR) or mass spectrometry (MS). NMR shifts (δ) are given in parts per million (ppm) and only selected peaks are given. "mp" is melting point and is given in ° C. Column chromatography was carried out using the technique described by W. C. Still et al, J. Org. Chem. 1978, 43, 2923-2925 on Merck silica gel 60 (Art 9385). Compounds used as starting materials are either known compounds or compounds which can readily be prepared by methods known per se. UV-Spectra (FIGS. 12-19) were acquired on a Shimadzu UV-1601(PC) in a ~$10^{-6}$M concentration of the quencher dissolved in methanol. The synthetic routes are illustrated in FIGS. 1-9.

Example 1

Preparation of 1-(3-(2-cyanoethoxy(diisopropylamino)phosphinoxy)-propylamino)-4-(3-(4,4'-d/ methoxy-trityloxy)propylamino)-anthraquinone (3)

1,4-Bis(3-hydroxypropylamino)-anthraquinone (1)

Leucoquinizarin (9.9 g; 0.04 mol) is mixed with 3-amino-1-propanol (10 mL) and Ethanol (200 mL) and heated to reflux for 6 hours. The mixture is cooled to room temperature and stirred overnight under atmospheric conditions. The mixture is poured into water (500 mL) and the precipitate is filtered off washed with water (200 mL) and dried. The solid is boiled in ethylacetate (300 mL), cooled to room temperature and the solid is collected by filtration.
Yield: 8.2 g (56%).

1-(3-(4,4'-dimethoxy-trityloxy)propylamino)-4-(3-hydroxypropylamino)-anthraguinone (2)

1,4-Bis(3-hydroxypropylamino)-anthraquinone (7.08 g; 0.02 mol) is dissolved in a mixture of dry N,N-dimethylformamide (150 mL) and dry pyridine (50 mL). Dimethoxytritylchloride (3.4 g; 0.01 mol) is added and the mixture is stirred for 2 hours. Additional dimethoxytritylchloride (3.4 g; 0.01 mol) is added and the mixture is stirred for 3 hours. The mixture is concentrated under vacuum and the residue is redissolved in dichloromethane (400 mL) washed with water (2×200 ml) and dried (Na$_2$SO$_4$). The solution is filtered through a silica gel pad (ø 10 cm; h 10 cm) and eluted with dichloromethane until mono-DMT-anthraquinone product begins to elute where after the solvent is the changed to 2% methanol in dichloromethane. The pure fractions are combined and concentrated resulting in a blue foam. Yield: 7.1 g (54%). $^1$H-NMR(CDCl$_3$): 10.8 (2H, 2×t, J=5.3 Hz, NH), 8.31 (2H, m, AqH), 7.67 (2H, dt, J=3.8 and 9.4, AqH), 7.4-7.1 (9H, m, ArH+AqH), 6.76 (4H, m, ArH) 3.86 (2H, q, J=5.5 Hz, CH$_2$OH), 3.71 (6H, s, CH$_3$), 3.54 (4H, m, NCH$_2$), 3.26 (2H, t, J=5.7 Hz, CH$_2$ODMT), 2.05 (4H, m, CCH$_2$C), 1.74 (1H, t, J=5 Hz, OH).

1-(3-(2-cyanoethoxy(diisopropylamino)phosphinoxy)propylamino)-4-(3-(4,4'-dimethoxy-trityloxy) propylamino)-anthraquinone (3)

1-(3-(4,4'-dimethoxy-trityloxy)propylamino)-4-(3-hydroxypropylamino)-anthraquinone (0.66 g; 1.0 mmol) is dissolved in dry dichloromethane (100 mL) and added 3 Å molecular sieves. The mixture is stirred for 3 hours and then added 2-cyanoethyl-N,N,N',N'-tetraisopropylphosphordiamidite (335 mg; 1.1 mmol) and 4,5-dicyanoimidazole (105 mg; 0.9 mmol). The mixture is stirred for 5 hours and then added sat. NaHCO$_3$ (50 mL) and stirred for 10 minutes. The phases are separated and the organic phase is washed with sat. NaHCO$_3$ (50 mL), brine (50 mL) and dried (Na$_2$SO$_4$). After concentration the phosphoramidite is obtained as a blue foam and is used in oligonucleotide synthesis without further purification. Yield: 705 mg (82%). $^{31}$P-NMR (CDCl$_3$): 150.0. $^1$H-NMR(CDCl$_3$): 10.8 (2H, 2×t, J=5.3 Hz, NH), 8.32 (2H, m, AqH), 7.67 (2H, m, AqH), 7.5-7.1 (9H, m, ArH+AqH), 6.77 (4H, m, ArH) 3.9-3.75 (4H, m,), 3.71 (6H, s, OCH$_3$), 3.64-3.52 (3.54 (6H, m), 3.26 (2H, t, J=5.8 Hz, CH$_2$ODMT), 2.63 (2H, t, J=6.4 Hz, CH$_2$CN) 2.05 (4H, m, CCH$_2$C), 1.18 (12H, dd, J=3.1 Hz, CCH$_3$).

Example 2

Preparation of 1-(3-(cyanoethoxy(diisopropylamino) phosphinoxy)propylamino)-5-(3-(4,4'-dimethoxytrityloxy)propylamino)-anthraquinone (6)

1,5-Bis(3-hydroxypropylamino)-anthraquinone (4)

1,5-Dichloroanthraquinone (2.8 g; 10 mmol) is mixed with 3-amino-1-propanol (10 mL) in DMSO (50 mL) and heated to 130° C. for 4 hours. The mixture is cooled to ~80° and added water (150 mL). When the mixture has reached RT the formed precipitate is isolated by filtration, washed with water (2×50 mL), boiled in toluene (200 mL) and the un-dissolved product is isolated by filtration and dried. Yield: 3.2 g (90%).

1-(3-hydroxypropylamino)-5-(3-(4,4'-dimethoxy-trityloxy)propylamino)-anthraquinone (5)

1,5-Bis(3-hydroxypropylamino)-anthraquinone (1.4 g; 4 mmol) is co-evapourated with pyridine (50 mL) and then resuspended in pyridine (50 mL) added dimethoxytritylchloride (1.4 g; 4.1 mmol) and stirred overnight. The mixture is concentrated and the residue redissolved in dichloromethane (150 mL), washed with sat. NaHCO$_3$ (2×50 mL), brine (50 mL), dried (Na$_2$SO$_4$) and concentrated. Purify on silica gel column (MeOH/dichloromethane 2/98). After concentration of the appropriate fractions the mono-DMT compound is obtained as a red foam. Yield: 0.9 g (34%). $^1$H-NMR(CDCl$_3$): 9.7 (2H, 2×t, NH), 7.6-6.7 (19H, m, ArH), 3.86 (2H, q, J=5.5 Hz, CH$_2$), 3.74 (6H, s, CH$_3$), 3.48 (4H, m, NCH$_2$), 3.26 (2H, t, J=5, 9 Hz), 2.05 (4H, m, CH$_2$), 1.45 (1H, t, J=5 Hz).

1-(3-(cyanoethoxy(diisopropylamino)phosphinoxy) propylamino)-5-(3-(4,4'-dimethoxy-trityloxy)propylamino)-anthraquinone (6)

1-(3-hydroxypropylamino)-5-(3-(4,4'-dimethoxy-trityloxy)propylamino)-anthraquinone (0.4 g; 0.61 mmol) is dissolved in dry dichloromethane (50 mL) and added 3 Å molecular sieves. The mixture is stirred for 3 hours and then added 2-cyanoethyl-N,N,N',N'-tetraisopropylphordiamidite (200 mg; 0.66 mmol) and 4,5-dicyanoimidazole (71 mg; 0.6 mmol). The mixture is stirred for 2 hours and then added sat. NaHCO$_3$ (50 mL) and stirred for 10 minutes. The phases are separated and the organic phase is washed with sat. NaHCO$_3$ (50 mL), brine (50 mL) and dried (Na$_2$SO$_4$). After concentration the phosphoramidite is obtained as a red foam and is used in oligonucleotide synthesis without further purification. Yield: 490 mg (93%). $^{31}$P-NMR (CDCl$_3$): 148.3.

Example 3

Preparation of 1-(4-(2-(2-cyanoethoxy(diisopropylamino)phosphinoxy)ethyl)phenylamino)-4-(4-(2-(4,4'-dimethoxy-trityloxy)ethyl)phenylamino)-anthraquinone (9)

1,4-Bis(4-(2-hydroethyl)phenylamino)-anthraquinone (7)

Leucoquinizarin (2.5 g; 0.01 mol) is mixed with boric acid (1.9 g; 0.03 mol) and ethanol (100 mL) and heated to reflux for 1 hour. The mixture is cooled to room temperature and added 4-aminophenethyl alcohol (4.1 g; 0.03 mol) where after the mixture is heated to reflux for 3 days. The mixture concentrated redissolved in dichloromethane (300 mL) washed with water (3×100 mL), dried ($Na_2SO_4$) and concentrated. The residue is purified on silica gel column with MeOH/dichloromethane (1/19). After concentration of the appropriate fractions the compound is obtained as a blue solid. Yield: 1.5 g (31%). $^1$H-NMR(DMSO-$d_6$): 12.2 (2H, s, NH), 8.31 (2H, dd, J=3.1 and 6.0 Hz, AqH), 7.88 (2H, dd, = 3.1 and 6.0 Hz, AqH), 7.59 (2H, s, AqH), 7.27 (2H, d, 3=2.7 Hz, ArH), 4.67 (2H, t, J=5.2 Hz, OH), 3.63 (4H, dt, =5.2 and 7.1 Hz, $CH_2O$), 2.74 (4H, t, J=7.1 Hz, $ArCH_2$).

1-(4-(2-(4,4'-dimethoxy-trityloxy)ethyl)phenylamino)-4-(4-(2-hydroethyl)phenylamino)-anthraquinone (8)

1,4-Bis(4-(2-hydroethyl)phenylamino)-anthraquinone (0.950 g; 2 mmol) is dissolved in a mixture of dry N,N-dimethylformamide (25 mL) and dry pyridine (5 mL). Dimethoxy-tritylchloride (0.34 g; 1 mmol) is added and the mixture is stirred for 2 hours. Additional dimethoxytritylchloride (0.34 g; 1 mmol) is added and the mixture is stirred for 4 hours. The mixture is concentrated under vacuum and the residue is redissolved in dichloromethane (200 mL) washed with water (2×100 ml) and dried ($Na_2SO_4$). The solution is filtered through a silica gel pad (ø 10 cm; h 10 cm) and eluted with dichloromethane until mono-DMT-anthraquinone product begins to elude where after the solvent is the changed to 1% methanol in dichloromethane. The pure fractions are combined and concentrated resulting in a blue solid. Yield: 0.81 g (52%). $^1$H-NMR($CDCl_3$): 12.2 (2H, s, NH), 8.38 (2H, dd, J=3.4 and 6.0 Hz, AqH), 7.75 (2H, dd, J=3.4 and 6.0 Hz, AqH), 7.46 (2H, s, AqH), 7.4-7.1 (17H, m, ArH), 6.8 (4H, m, ArH), 3.63 (2H, dt, J=5.8 and 6.6 Hz, $CH_2O$), 3.75 (2H, s, $CH_3$), 3.33 (2H, t, J=6.6 Hz, $CH_2ODMT$), 2.88 (4H, t, J=6.6 Hz, $ArCH_2$), 1.42 (1H, t, J=5.8 Hz, OH).

1-(4-(2-(2-cyanoethoxy(diisopropylamino)phosphinoxy)ethyl)phenylamino)-4-(4-(2-(4,4'-dimethoxytrityloxy)ethyl)phenylamino)-anthraquinone (9)

1-(4-(2-(4,4'-dimethoxy-trityloxy)ethyl)phenylamino)-4-(4-(2-hydroethyl)phenylamino)-anthraquinone (0.50 g; 0.64 mmol) is dissolved in dry dichloromethane (50 mL) and added 3 Å molecular sieves. The mixture is stirred for 3 hours and then added 2-cyanoethyl-N,N,N',N'-tetraisopropylphosphordiamidite (215 mg; 0.72 mmol) and 4,5-dicyanoimidazole (64 mg; 0.55 mmol). The mixture is stirred for 4 hours and then added sat. $NaHCO_3$ (25 mL) and stirred for 10 minutes. The phases are separated and the organic phase is washed with sat. $NaHCO_3$ (25 mL), brine (25 mL) and dried ($Na_2SO_4$). After concentration the phosphoramidite is obtained as a blue foam and is used in oligonucleotide synthesis without further purification. Yield: 0.59 g (94%).

Example 4

Preparation of 1-(3-(2-Cyanoethoxy(diisopropylamino)phosphinoxy)-propylamino)-4-(3-(4,4'-dimethoxy-trityloxy)propylamino)-6(7)-methyl-anthraquinone (13)

6-methyl-Quinizarin (10)

4-methyl-phthalic anhydride (10 g, 62 mmol), p-chlorophenol (3.6 g, 28 mmol) and Boric acid (1.6 g) were dissolved in concentrated $H_2SO_4$ (34 ml) and the mixture was stirred at 200° C. for 6 hours in a flask covered with a glass plate. After completion of the reaction, the mixture was allowed to cool and then poured into water (160 ml) and the precipitate collected by filtration. The solid was suspended in boiling water (320 ml) and boiled for 5 min, whereupon the solid was collected by filtration. The product was obtained as a dark red solid (5 g, 19.7 mmol) after drying. MALDI-MS: m/z 255.7 (M+H).

1,4-Bis(3-hydroxypropylamino)-6-methylanthraquinone (11)

6-methyl-quinizarin was dissolved in ethanol (35 ml) and 3-aminopropanol (15 ml) was added and the mixture was refluxed for 6 hours. After completion, the reaction mixture was cooled to room temperature and poured into water (300 ml) and extracted with dichloromethane. The organic phase was evaporated to dryness and subsequently purified by column chromatography affording the diol as a blue oil (~1 g, ~2.7 mmol) Rf: 0.12 (5% MeOH/DCM) MALDI-MS: 369.5 (M+H).

1-(3-(4,4'-dimethoxy-trityloxy)propylamino)-4-(3-hydroxypropylamino)-6(7)-methylanthraquinone (12)

To a solution of 1,4-Bis(3-hydroxypropylamino)-6-methylanthraquinone (0.5 g, 1.36 mmol) in anhydrous pyridine (30 ml) was added 4,4'-dimethoxytritylchloride (500 mg, 1.48 mmol) and the reaction mixture was stirred under inert atmosphere for ½ h, whereupon the reaction was quenched by addition of $NaHCO_3$ (30 ml) and diluted with dichloromethane (100 ml). The phases were separated and the organic phase was washed with brine (30 ml), dried ($Na_2SO_4$) and evaporated to dryness. The residue was coevaporated with toluene to remove pyridine. The mono-DMT protected anthraquinone was purified by column chromatography (0-1% MeOH/dichloromethane containing 0.1% triethylamine) affording the compound as a blue solid (100 mg, 0.15 mmol). MALDI-MS: 670 (M$^+$)

1-(3-(2-cyanoethoxy(diisopropylamino)phosphinoxy)propylamino)-4-(3-(4,4'-dimethoxy-trityloxy) propylamino)-6(7)-methyl-anthraquinone (13)

The mono-DMT protected compound (100 mg, 0,15 mmol) was dissolved in anhydrous dichloromethane (30 ml), 3 Å molecular sieves were added and the mixture was stirred overnight under inert atmosphere. 4,5-Dicyanoimidazole (38 mg, 32 mmol) was suspended in anhydrous dichloromethane (6 ml) and 2-cyanoethyl-N,N,N',N'-tetraisopropylphosphoramidite (11 mg, 0.36 mmol) was added and the mixture was stirred for 10 min at room temperature. Thereafter, this mixture was transferred to the flask containing the anthraquinone derivative and the mixture was allowed to stir for 30 min at room temperature. After completion of the reaction, NaHCO$_3$ (saturated solution, 50 ml) was added and the phases were separated. The organic phase was subsequently washed with NaHCO$_3$ (50 ml) and brine (50 ml). The organic phase was dried (Na$_2$SO$_4$), evaporated to dryness and finally co-evaporated with anhydrous acetonitrile affording the amidite as a blue oil (80 mg, 0.09 mmol), which was used for oligonucleotide synthesis without any further purification. MALDI-MS: m/z=869 (M+).

Example 5

Preparation of 1,4-Bis(4-(2-hydroethyl)phenylamino)-6-methyl-anthraquinone (15)

6-Methyl-quinizarin (1 g, mmol) was mixed with Zn-dust (2 g) in acetic acid (150 ml) and stirred for 2½ h at 90° C. where after the reaction was filtered through a thin layer of celite. The product precipitated by addition of water and was subsequently collected by filtration and washed with water (300 ml). The reduced anthraquinone derivative was subsequently dissolved in n-pentanol (50 ml). Boric acid (2 g), phenetylamine (2 g) and Na$_2$O$_4$S$_2$ (2 g) was added and the mixture was stirred at 120° C. for 4 days where after the mixture was pored into water and the mixture was extracted with dichloromethane (100 ml). The organic phase was washed with brine, dried (Na$_2$SO$_4$) and evaporated to dryness. The product was purified by column chromatography (0-2% MeOH/dichloromethane) affording the 1,4-amino-substituted anthraquinone derivative as a blue/green solid (0.1 g). MALDI-MS: 493.4 (M+H)

Example 6

Preparation of 1,4-bis(4-methyl-phenylamino)-6-(N-(7-(2-cyanoethoxy-(diisopropylamino)phosphinoxy)-6-hydroxy-4-oxo-heptane-1-yl))carboxamido-anthraquinone (19)

1,4-Dihydroxy-2,3-dihydro-6-carboxy-anthraquinone (16)

1,4-Dihydroxy-anthraquinone-6-carboxylic acid (1.5 g) is mixed with Zn dust (3 g) in 300 mL glacial Acetic acid. The mixture is heated to 100° C. for 2 hours, filtered through Celite concentrated to half volume and added 250 mL water and placed at 5° C. overnight. The precipitate is collected by filtration. Yield: 1.1 g.

1,4-Bis(4-methyl-phenylamino)-6-carboxy-anthraquinone (17)

1,4-Dihydroxy-2,3-dihydro-6-carboxy-anthraquinone (300 mg) Boric acid (300 mg) and p-Toluidine (1.8 g) is mixed in n-pentanol (5 mL) and heated to 110° C. for 4 hours, the residue is co-evaporated with 2×50 ml of water. The residue is redissolved in dichloromethane/THF (1/1) 200 ml washed with water (3×100 mL) dried (Na$_2$SO$_4$), filtered and concentrated. The residue is purified on a silicagel column (CH$_2$Cl$_2$/MeOH/NEt$_3$; 90/9/1) resulting in 350 mg of pure material. MALDI-MS: m/z 463.2 (M+H)

1,4-Bis(4-methyl-phenylamino)-6-(N-(7-dimethoxytrityloxy-6-hydroxy-4-oxo-heptane-1-yl))carboxamido-anthraquinone (18)

1,4-Bis(4-methyl-phenylamino)-6-carboxy-anthraquinone (155 mg) is dissolved in mixed CH$_2$Cl$_2$ (10 mL) added NEt$_3$ (0.5 mL) and benzotriazol-1-yloxy-tris(dimethylamino)-phosohonium hexafluorophosphate (200 mg) and stirred for 15 minutes. 7-(Dimethoxytrityloxy)-6-hydroxy-4-oxa-heptylamine (220 mg) is added and the mixture is stirred for 2 hours. The mixture is purified on a silicagel column (CH$_2$Cl$_2$/EtOAc/NEt$_3$; 89/10/1) resulting in 210 mg of a green foam. MALDI-MS: m/z 895.6 (M+H)

1,4-Bis(4-methyl-phenylamino)-6-(N-(7-(2-cyanoethoxy(diisopropylamino)phosphinoxy)-6-hydroxy-4-oxo-heptane-1-yl))carboxamido-anthraquinone (19)

1,4-Bis(4-methyl-phenylamino)-6-(N-(7-dimethoxytrityloxy-6-hydroxy-4-oxo-heptane-1-yl))carboxamido-anthraquinone (150 mg) is dissolved in dry dichloromethane (15 mL) and added 3 Å molecular sieves. The mixture is stirred for 3 hours and then added 2-cyanoethyl-N,N,N',N'-tetraisopropylphosphordiamidite (55 mg) and 4,5-dicyanoimidazole (15 mg; 0.55 mmol). The mixture is stirred for 4 hours and then added sat. NaHCO$_3$ (10 mL) and stirred for 10 minutes. The phases are separated and the organic phase is washed with sat. NaHCO$_3$ (10 mL), brine (10 mL) and dried (Na$_2$SO$_4$). After concentration the phosphoramidite is obtained as a blue/green foam and is used in oligonucleotide synthesis without further purification.

Example 7

Preparation of 1-(4-(2-(cyanoethoxy(diisopropylamino)phosphinoxy)ethyl)-phenylamino)-5-(4-(2-(4,4'-dimethoxy-trityloxy)ethyl)phenylamino)-anthraquinone (22)

1,5-Bis(4-(2-hydroethyl)phenylamino)-anthraquinone (20)

1,5-Dinitroanthraquinone (3.0 g; 10 mmol) is mixed with 4-aminophenethyl alcohol (6 g) in DMSO (50 mL) and heated to 130° C. for 4 hours. The mixture is cooled and added water (150 mL). The precipitate is isolated by filtration, washed with water (2×50 mL), dried and purified on silicagel column (CH$_2$Cl$_2$ 0-10% MeOH). Yield: 1.2 g (25%). MALDI-MS: m/z 479.4 (M+H).

1-(4-(2-hydroethyl)phenylamino)-5-(4-(2-(4,4'-dimethoxy-trityloxy)ethyl)phenylamino)-anthraquinone (21)

1,5-Bis(4-(2-hydroethyl)phenylamino)-anthraquinone (960 mg; 2 mmol) is co-evaporated with pyridine (25 mL) and then resuspended in pyridine (25 mL) added dimethoxytritylchloride (680 mg; 2 mmol) and stirred overnight. The mixture is concentrated and the residue redissolved in dichloromethane (150 mL), washed with sat. NaHCO$_3$ (2×50 mL), brine (50 mL), dried (Na$_2$SO$_4$) and concentrated. Purify on silica gel column (MeOH/dichloromethane 2/98). Yield: 395 mg (24%) MALDI-MS: m/z 780.9 (M+H)

1-(4-(2-(cyanoethoxy(diisopropylamino)phosphi-
noxy)ethyl)phenylamino)-5-(4-(2-(4,4'-dimethoxy-
trityloxy)ethyl)phenylamino)-anthraquinone (22)

1-(4-(2-hydroethyl)phenylamino)-5-(4-(2-(4,4'-dimethoxy-trityloxy)ethyl)phenylamino)-anthraquinone (0.350 mg; 0.44 mmol) is dissolved in dry dichloromethane (15 mL) and added 3 Å molecular sieves. The mixture is stirred for 3 hours and then added 2-cyanoethyl-N,N,N',N'-tetraisopropylphosphordiamidite (150 mg; 0.5 mmol) and 4,5-dicyanoimidazole (50 mg; 0.4 mmol). The mixture is stirred for 3 hours and then added sat. $NaHCO_3$ (25 mL) and stirred for 10 minutes. The phases are separated and the organic phase is washed with sat. $NaHCO_3$ (25 mL), brine (25 mL) and dried ($Na_2SO_4$). After concentration the phosphoramidite is obtained as a dark red foam and is used in oligonucleotide synthesis without further purification. Yield: 410 mg.

Example 8

Preparation of 1-(3-(cyanoethoxy(diisopropylamino)
phosphinoxy)propylamino)-8-(3-(4,4'-dimethoxy-
trityloxy)propylamino)-anthraquinone (25)

1,8-Bis(3-hydroxypropylamino)-anthraquinone (23)

1,8-Dinitrochloroanthraquinone (3 g; 10 mmol) is mixed with 3-amino-1-propanol (10 mL) in DMSO (50 mL) and heated to 130° C. for 4 hours. The mixture is cooled and added water (150 mL), the formed precipitate is isolated by filtration, washed with water (2×50 mL) dried and purified on silicagel column ($CH_2Cl_2$ 0-10% MeOH). Yield: 2.8 g (78%) of a purple solid. MALDI-MS: m/z 355.4 (M+H).

1-(3-hydroxypropylamino)-8-(3-(4,4-dimethoxy-
trityloxy)propylamino)-anthraquinone (24)

1,8-Bis(3-hydroxypropylamino)-anthraquinone (1.4 g; 4 mmol) is co-evapourated with pyridine (50 mL) and then resuspended in pyridine (50 mL) added dimethoxytritylchloride (1.4 g; 4 mmol) and stirred overnight. The mixture is concentrated and the residue redissolved in dichloromethane (100 mL), washed with sat. $NaHCO_3$ (2×50 mL), brine (50 mL), dried ($Na_2SO_4$) and concentrated.
Purify on silica gel column (MeOH/dichloromethane 2/98). After concentration of the appropriate fractions the mono-DMT compound is obtained as purple foam. Yield: 1.1 (42%) MALDI-MS: m/z 657 (M+H).

1-(3-(cyanoethoxy(diisopropylamino)phosphinoxy)
propylamino)-8-(3-(4,4'-dimethoxy-trityloxy)propy-
lamino)-anthraquinone (25)

1-(3-hydroxypropylamino)-8-(3-(4,4-dimethoxy-trityloxy)propylamino)-anthraquinone (0.4 g; 0.61 mmol) is dissolved in dry dichloromethane (50 mL) and added 3 Å molecular sieves. The mixture is stirred for 3 hours and then added 2-cyanoethyl-N,N,N',N'-tetraisopropylphosphordiamidite (200 mg; 0.66 mmol) and 4,5-dicyanoimidazole (70 mg; 0.6 mmol). The mixture is stirred for 2 hours and then added sat. $NaHCO_3$ (50 mL) and stirred for 10 minutes. The phases are separated and the organic phase is washed with sat. $NaHCO_3$ (50 mL), brine (50 mL) and dried ($Na_2SO_4$). After concentration the phosphoramidite is obtained as purple foam and is used in oligonucleotide synthesis without further purification. Yield: 440 mg (85%).

Example 9

Preparation of 1-(4-(2-(cyanoethoxy(diisopropy-
lamino)phosphinoxy)ethyl)-phenylamino)-8-(4-(2-
(4,4'-dimethoxytrityloxy)ethyl)phenylamino)-an-
thraquinone (28)

1,8-Bis(4-(2-hydroethyl)phenylamino)-anthraquinone (26)

1,8-Dinitroanthraquinone (3.0 g; 10 mmol) is mixed with 4-aminophenethyl alcohol (6 g) in DMSO (50 mL) and heated to 130° C. for 4 hours. The mixture is cooled and added water (150 mL). The precipitate is isolated by filtration, washed with water (2×50 mL), dried and purified on silicagel column ($CH_2Cl_2$ 0-10% MeOH). Yield: 1.2 g (20%). MALDI-MS: m/z 479.2 (M+H).

1-(4-(2-hydroethyl)phenylamino)-8-(4-(2-(4,4'-
dimethoxy-trityloxy)ethyl)phenylamino)-an-
thraquinone (27)

1,8-Bis(4-(2-hydroethyl)phenylamino)-anthraquinone (480 mg; 1 mmol) is co-evapourated with pyridine (25 mL) and then resuspended in pyridine (25 mL) added dimethoxytrityl-chloride (340 mg; 1 mmol) and stirred overnight. The mixture is concentrated and the residue redissolved in dichloromethane (150 mL), washed with sat. $NaHCO_3$ (2×50 mL), brine (50 mL), dried ($Na_2SO_4$) and concentrated. Purify on silica gel column (MeOH/dichloromethane 2/98). Yield: 220 mg (28%) of a dark purple foam. MALDI-MS: m/z 780.7 (M+H).

1-(4-(2-(cyanoethoxy(diisopropylamino)phosphi-
noxy)ethyl)phenylamino)-8-(4-(2-(4,4'-dimethoxy-
trityloxy)ethyl)phenylamino)-anthraquinone (28)

1-(4-(2-hydroethyl)phenylamino)-8-(4-(2-(4,4'-dimethoxy-trityloxy)ethyl)phenylamino)-anthraquinone (0.200 mg; 0.25 mmol) is dissolved in dry dichloromethane (10 mL) and added 3 Å molecular sieves. The mixture is stirred for 3 hours and then added 2-cyanoethyl-N,N,N',N'-tetraisopropylphosphordiamidite (90 mg; 0.3 mmol) and 4,5-dicyanoimidazole (25 mg; 0.2 mmol). The mixture is stirred for 3 hours and then added sat. $NaHCO_3$ (25 mL) and stirred for 10 minutes. The phases are separated and the organic phase is washed with sat. $NaHCO_3$ (25 mL), brine (25 mL) and dried ($Na_2SO_4$). After concentration the phosphoramidite is obtained as a dark red/purple foam and is used in oligonucleotide synthesis without further purification. Yield: 220 mg.

Example 10

Synthesis, Deprotection and Purification of Dual Labelled Oligonucleotides

The dual labelled oligonucleotides were prepared on an automated DNA synthesizer (Expedite 8909 DNA synthesizer, PerSeptive Biosystems, 0.2 μmol scale) using the phosphoramidite approach (Beaucage and Caruthers, *Tetrahedron Lett.* 22: 1859-1862, 1981) with 2-cyanoethyl protected LNA and DNA phosphoramidites, (Sinha, et al., *Tetrahedron Lett.* 24: 5843-5846, 1983), C PG-Phosphate solid supports and 5'-fluorescein phosphoramidite (GLEN Research, Sterling, Va., USA). The synthesis cycle was modified for LNA phosphoramidites and quencher phosphoramidites (250 s coupling time) compared to DNA phosphoramidites. 1H-tetrazole or 4,5-dicyanoimidazole (Proligo, Hamburg, Germany) was used as activator in the coupling step.

The oligonucleotides were deprotected using 32% aqueous ammonia (1 h at room temperature, then 2 hours at 60° C.) and purified by HPLC (Shimadzu-SpectraChrom series; Xterra™ RP18 column, 10 μm 7.8×150 mm (Waters). Buffers: A: 0.05 M Triethylammonium acetate pH 7.4. B. 50% acetonitrile in water. Eluent: 0-25 min: 10-80% B; 25-30 min: 80% B). The composition and purity of the oligonucleotides were verified by MALDI-MS (PerSeptive Biosystem, Voyager DE-PRO) analysis.

Example 11

Real Time PCR with Probes Synthesized with Quenchers Prepared as Described in Example 1 (Compound (3), Q1) or Example 2 (Compound (6), Q2)

Reagents for the Real Time dual label probe PCRs were mixed according to the following scheme (Table 1):

TABLE 1

PCR Setup

| Reagents | Final Concentration |
|---|---|
| H$_2$O | |
| GeneAmp 10× PCR buffer II | 1× |
| Mg$^{2+}$ | 3.5 mM |
| dNTP | 0.2 mM |
| Dual Label Probe | 0.1 μM |
| Template | 1 μL* |
| Forward primer | 0.2 μM |
| Reverse primer | 0.2 μM |
| AmpliTaq Gold | 2.5 U |
| Total | 50 μL |

*In the present experiments. 2 × 10$^7$ copies of the SSA4 cDNA were added as template.

The following primers and probes were included in the above mentioned PCR mix (Table 2).

Assays were performed in a DNA Engine Opticon® (MJ Research) using the following PCR cycle protocol (see Table 3).

TABLE 3

PCR-termocycling protocol

| | 95° C. for 7 minutes |
|---|---|
| 40 cycles of: | 94° C. for 20 seconds |
| | 60° C. for 1 minute |
| | Fluorescence detection |

Figure 10:
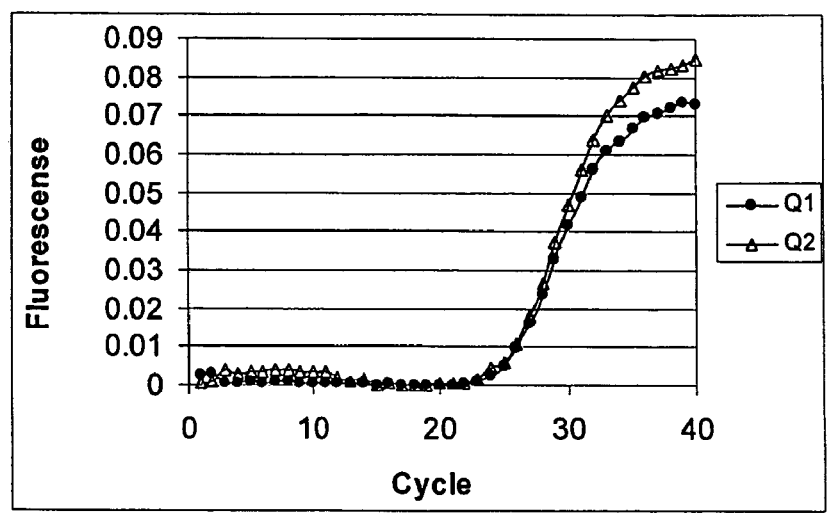
FIG. 10 illustrates the result from performing real time PCR with probes carrying either the Q1 (3) or the Q2 (6) quencher together with the fluorecein dye.

Results from the two Real Time PCRs are illustrated in FIG. 10, which shows that dual labelled probes with either of the two quenchers Q1 (3) and Q2 (6) are fully functional as real time PCR probes.

Production of of SSA4 cDNA for Detection with Dual Labelled Probes

The functionality of the constructed probes were analysed in PCR assays where the probes ability to detect different SSA4 PCR amplicons were questioned. Template for the PCR reaction was cDNA obtained from reverse transcription of cRNA produced from in vitro transcription of a downstream region of the SSA4 gene in the expression vector pTRIamp18 (Ambion). The downstream region of the SSA4 gene was cloned as follows:

PCR Amplification

Amplification of the partial yeast gene was done by standard PCR using yeast genomic DNA as template. Genomic DNA was prepared from a wild type standard laboratory strain of *Saccharomyces cerevisiae* using the Nucleon MIY DNA extraction kit (Amersham Biosciences) according to supplier's instructions. In the first step of PCR amplification, a forward primer containing a restriction enzyme site and a reverse primer containing a universal linker sequence were used. In this step 20 bp was added to the 3'-end of the amplicon, next to the stop codon. In the second step of amplification, the reverse primer was exchanged with a nested primer

TABLE 2

Probes and primers

| | | Name | Sequence (5'-3') |
|---|---|---|---|
| Forward Primer (SEQ ID NO. 1) | | 14012 SSA4-469-F | Cgcgtttactttgaaaaattctg |
| Reverse Primer (SEQ ID NO. 2) | | 14013 SSA4-469-R | Gcttccaatttcctggcatc |
| Q1 Dual Label Probe (SEQ ID NO. 3) | 14570 Q1 quench | | Fitc-tcaaggagaaggtgggtgaagagg-Q1-P |
| Q2 Dual Label Probe (SEQ ID NO. 3) | 14584 Q2 quench | | Fitc-tcaaggagaaggtgggtgaagagg-Q2-P |

Fitc is fluoroscein (FITC (Glenn Research, Prod.Id.No. 10-1964)). Lower case (a, t, c, g) designates natural nucleosides. P designates a phosphate group. Q1 designates the quencher (3) prepared as described in Example 1. Q2 designates the quencher (6) prepared as described in Example 2.

containing a poly-$T_{20}$ tail and a restriction enzyme site. The SSA4 amplicon contains 729 bp of the SSA4 ORF plus a 20 bp universal linker sequence and a poly-$A_{20}$ tail.

The PCR Primers Used Were:

```
                                           (SEQ ID NO. 4)
YER103W-For-SacI:
acgtgagctcattgaaactgcaggtggtattatga (SEQ ID NO. 5)
YER103W-Rev-Uni:
gatccccgggaattgccatgctaatcaacctcttcaaccgttgg (SEQ ID NO. 6)
Uni-polyT-BamHI:
acgtggatcctttttttttttttttttttgatcccgggaattgccatg
```

Plasmid DNA Constructs

The PCR amplicon was cut with the restriction enzymes, EcoRI+BamHI. The DNA fragment was ligated into the pTRIamp18 vector (Ambion) using the Quick Ligation Kit (New England Biolabs) according to the supplier's instructions and transformed into *E. coli* DH-5 by standard methods.

DNA Sequencing

To verify the cloning of the PCR amplicon, plasmid DNA was sequenced using M13 forward and M13 reverse primers and analysed on an ABI 377.

In Vitro Transcription

SSA4 cRNA was obtained by performing in vitro transcription with the Megascript T7 kit (Ambion) according to the supplier's instructions.

Reverse Transcription

Reverse transcription was performed with 1 μg of cRNA and 0.2 U of the reverse transcriptase Superscript II RT (Invitrogen) according to the suppliers instructions except that 20 U Superase-In (RNAse inhibitor—Ambion) was added. The produced cDNA was purified on a QiaQuick PCR purification column (Qiagen) according to the supplier's instructions using the supplied EB-buffer for elution. The DNA concentration of the eluted cDNA was measured and diluted to a concentration of SSA4 cDNA copies corresponding to $2 \times 10^7$ copies pr μL.

Example 12

Real Time PCR with Probes Carrying the Quencher (Compound (3), Q1) as an Internal Quencher Incorporated in a LNA/DNA Oligonucleotide The experiments were conducted essentially as in Example 11.

TABLE 4

Probes and primers

| Name | Sequence (5'-3') |
|---|---|
| Forward Primer (SEQ ID NO. 7) | EQ15910 | gtggtcgaaagcaatggact |
| Reverse Primer (SEQ ID NO. 8) | EQ15911 | gggattcgaaccettggtat |
| Q1Dual Label Probe (SEQ ID NO. 9) | EQ16234 | Fitc-cTGCCTCTQ1ttcctctg-P |

TABLE 4-continued

Probes and primers

| Name | Sequence (5'-3') |
|---|---|
| Target (SEQ ID NO. 10) | Gtggtcgaaagcaatggacttgcaggag gagcagaggaaagaggcagaaggagaag cccataccaagggttcgaatccc |

Fitc is fluoroscein (FITC (Glenn Research, Prod. Id. No. 10-1964)). Upper case (A, T, G, C) designates oxy-LNA, i.e. 2',4'-linked nucleotides carrying a 2',4'-oxymethylene linker. Lower case (a, t, c, g) designates natural nucleosides. P designates a phosphate group. Q1 designates the quencher (3) prepared as described in Example 1.

TABLE 5

PCR setup

| Reagents | Final Conc. |
|---|---|
| For Primer EQ-15910 | 0.9 μM |
| Rev Primer EQ-15911 | 0.9 μM |
| Probe (EQ-16234) | 0.2 μM |
| Qiagen Taq | 0.05 U/μL |
| MgCl$_2$ (additional) | 1.5 mM |
| dUTP | 200 μM |
| ROX (Invitrogen) | 0.1× |
| PCR-buffer (Qiagen, incl. 1.5 mM Mg$^{++}$) | 1× |
| Template | 4 pM |
| H$_2$O | |
| Final Volume (incl. Template) | 350 μL |

TABLE 6

PCR-termocycling protocol

| | 95° C. for 10 minutes |
|---|---|
| 40 cycles of: | 94° C. for 20 seconds |
| | 60° C. for 1 minute |
| | Fluorescence detection |

Figure 11:
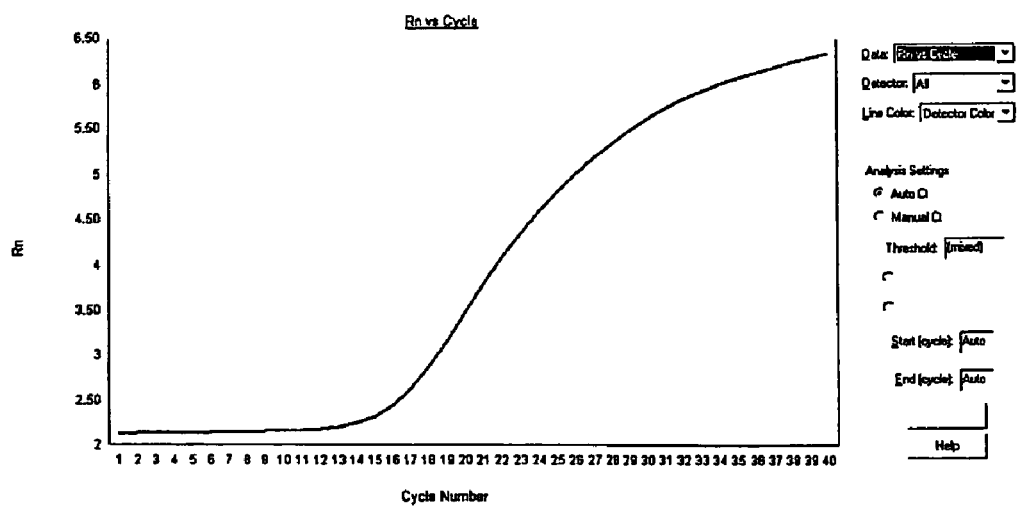
FIG. 11 illustrates the result from performing real time PCR with probes carrying the Q1 (3) as an internal quencher incorporated in a LNA/DNA oligonucleotide.
Figure 12:
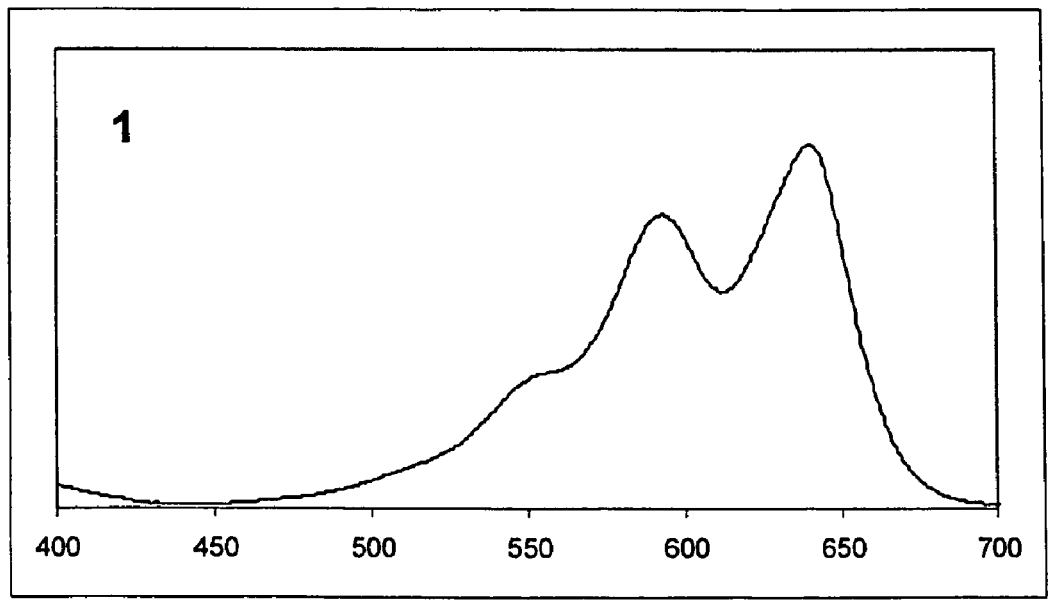
FIGS. 12-20 illustrate UV spectra for the quencers (1), (4), (7), (11), (15), (18), (20), (23) and (26).
Figure 13:
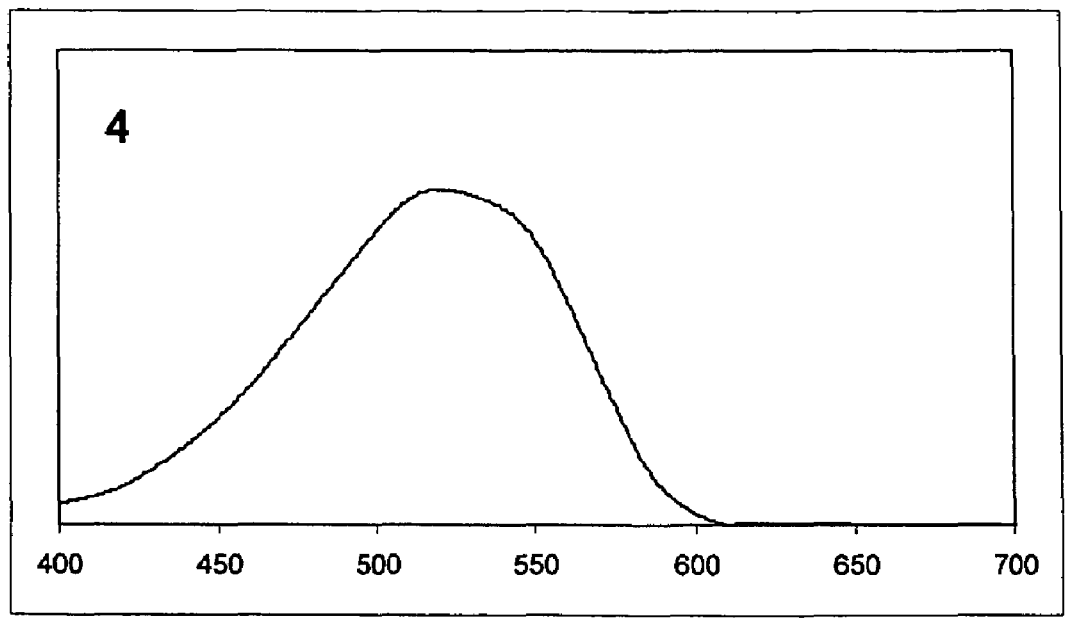
Figure 14:
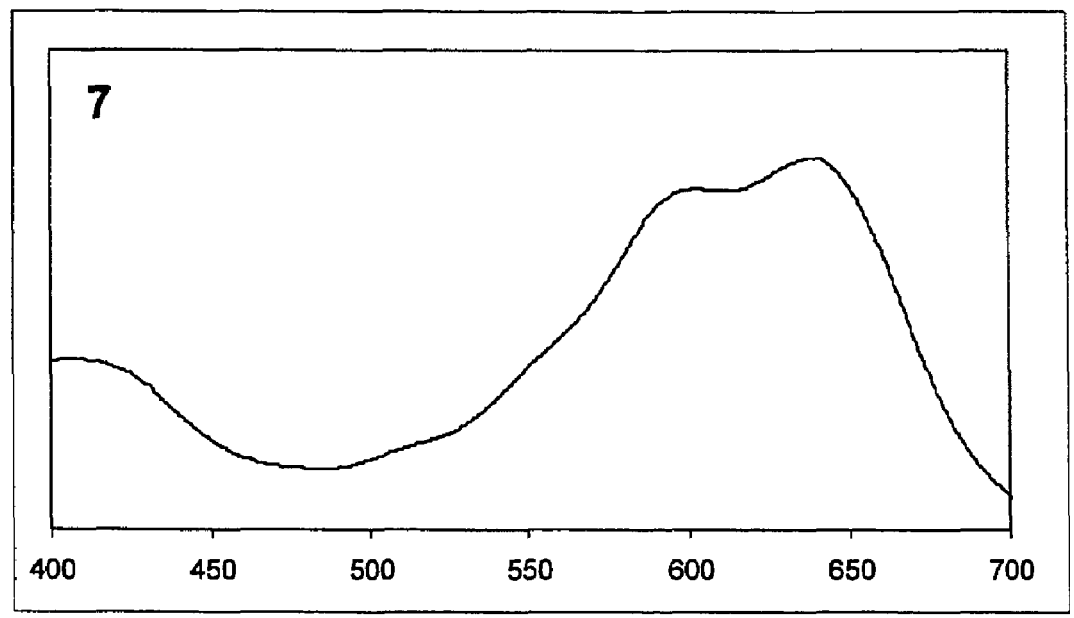
Figure 15:
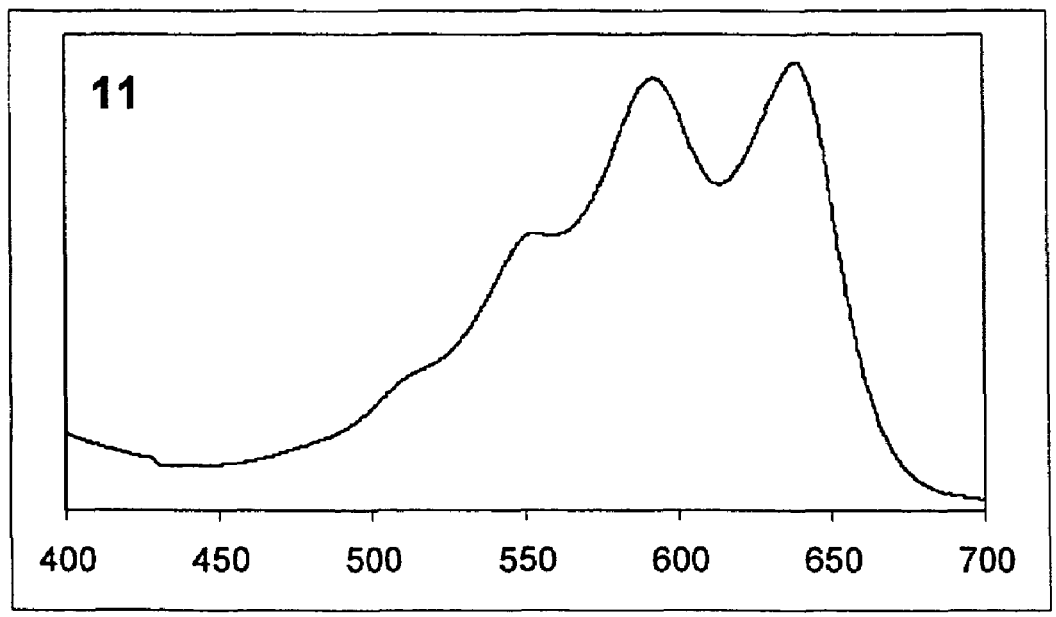
Figure 16:
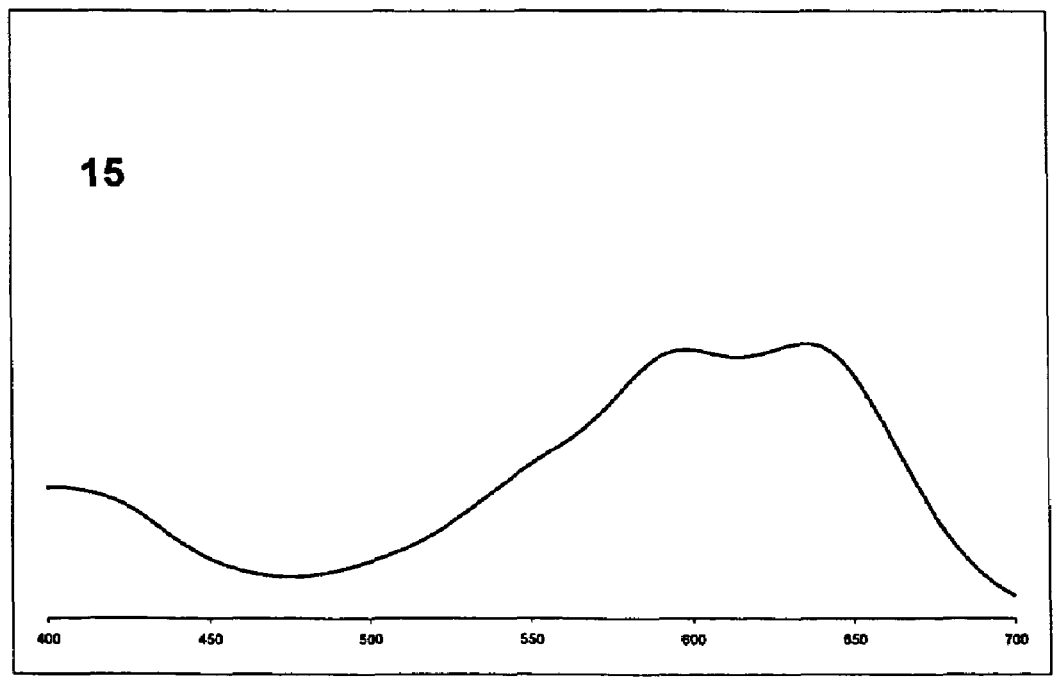
Figure 17:
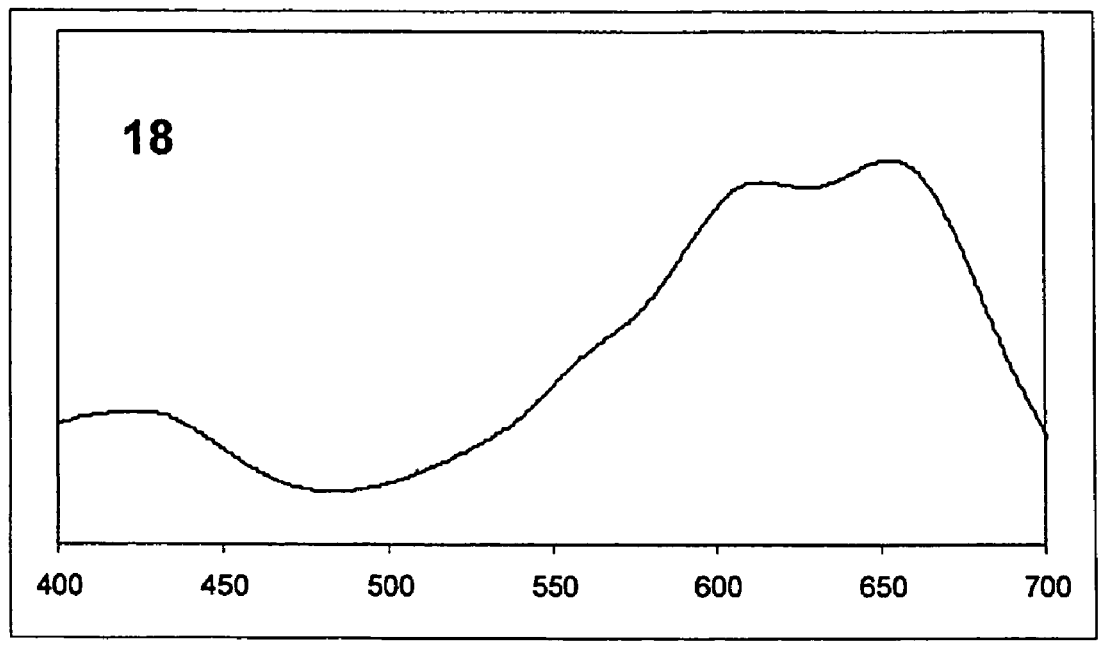
Figure 18:
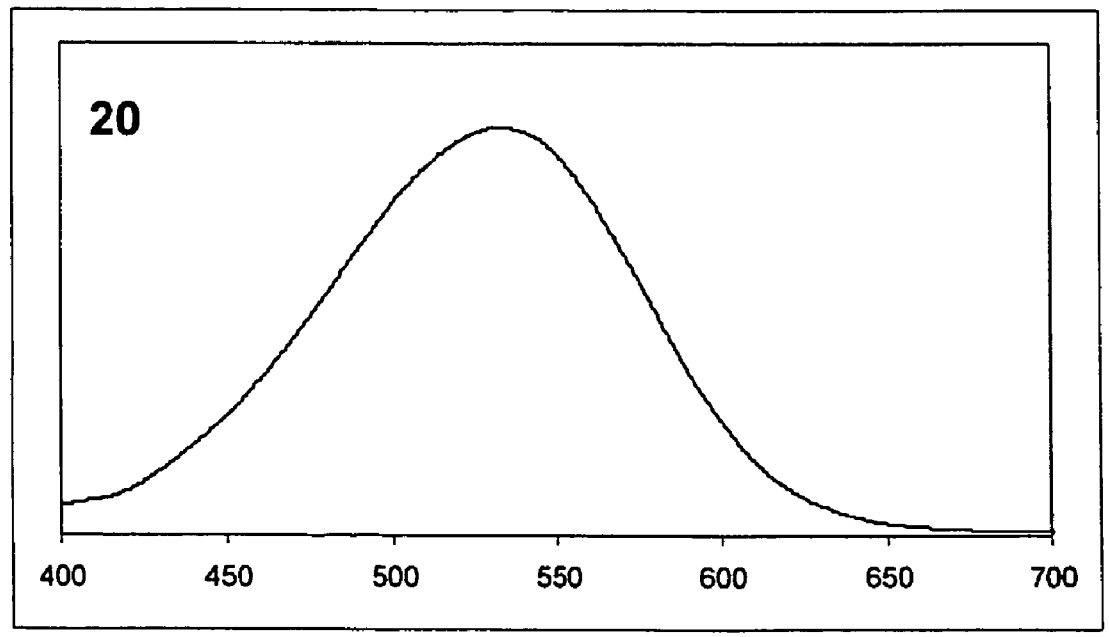
Figure 19:
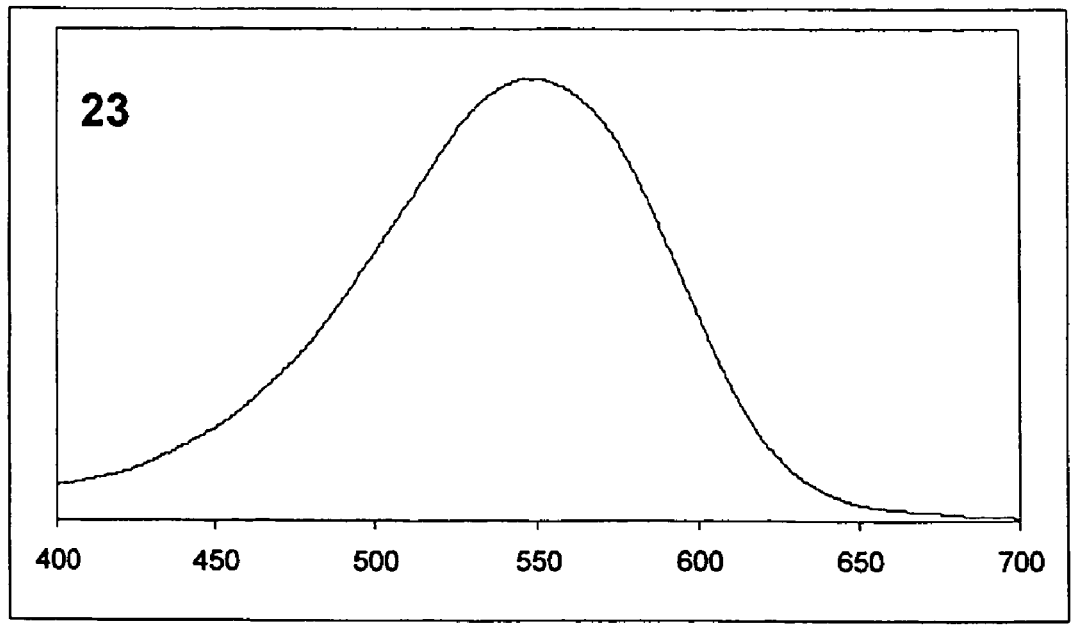
Figure 20:
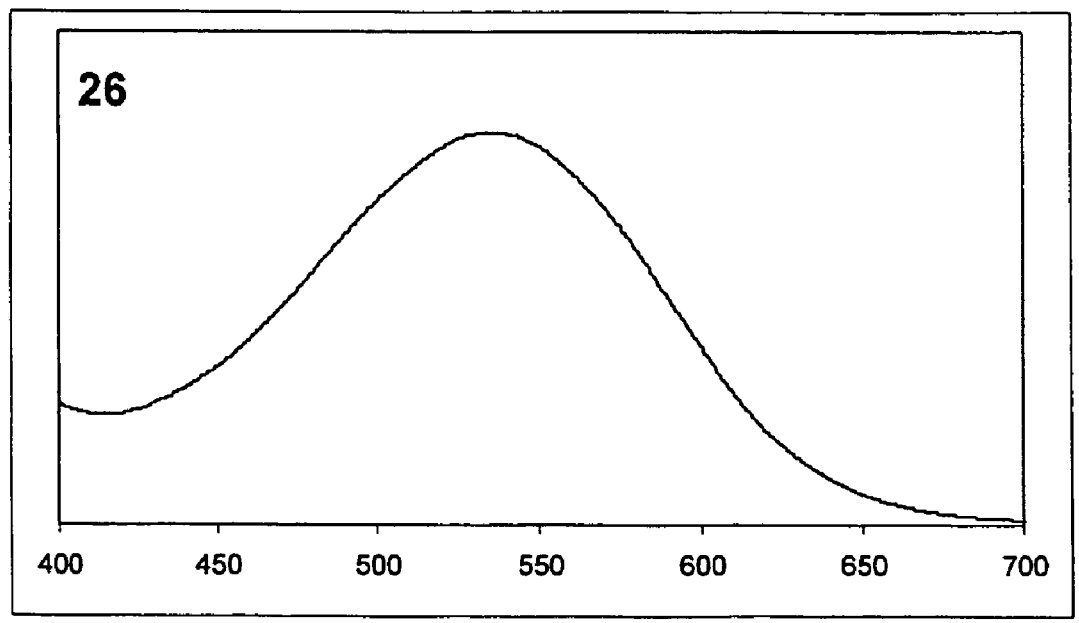

Results are shown in FIG. 11.

Embodiments

The invention can also be defined by means of the following embodiments, wherein the term "item" refers to a preceding item with the specified number.

1. A quencher composition of the formula (II):

$$Q-L^1-Y(-L^2-Z)-L^3-X \quad (II)$$

wherein Y is nitrogen or $$-\!\!\!\overset{|}{\underset{|}{C}}\!\!\!-R^9$$

wherein $R^9$ is hydrogen, $C_1$-$C_6$-alkyl, aryl, aryldiyl or aryltriyl; $L^1$, $L^2$ and $L^3$ are each, independently, a bond or a linker;

X is a biomolecule, a protected form thereof or an acid-labile or base labile protecting group; wherein the biomolecule is selected from an amino acid, a polypeptide, a nucleoside, a nucleotide or a polynucleotide and optionally further comprises a fluorophore; Z is a bond or selected from —H, —CO$_2$H, —OH, —NH$_2$, —NHR$^{10}$, or —N(R$^{10}$)$_2$, —SH, a phosphate, a nucleotide, a substituted nucleotide, a polynucleotide, a substituted polynucleotide, an ester, a cleavable linker, a solid support, a reactive linking group or a label; all of which are optionally substituted with a label or a solid support; and wherein R$^{10}$ is hydrogen, C$_1$-C$_6$ alkyl, aryl, aryldiyl, aryltriyl; Q is a compound of the formula (I)

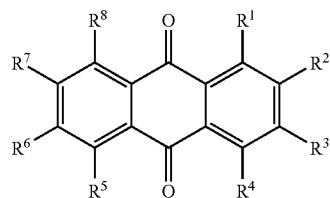

wherein at least one, two, three or four of R$^1$, R$^4$, R$^5$ or R$^8$ are each and independently selected from substituted or non-substituted amino-alkyl, amino-aryl or amino-alkylaryl and the remaining R$^1$ to R$^8$ groups are each and independently hydrogen or substituted or non-substituted hydroxy, amino, alkyl, aryl, arylalkyl or alkoxy; and wherein Q is attached to the linker L either through one of the α-amino groups or through one of the aryl carbons of the quencher moiety.

2. A compound of item 1 wherein L$^1$, L$^2$ and L$^3$ are each, independently selected from C$_1$-C$_{12}$-alkyldiyl, C$_1$-C$_{12}$-alkoxydiyl, alkylaryl, C$_1$-C$_{12}$-alkylaminodiyl, C$_1$-C$_{12}$-alkylamidediyl, aryldiyl or 1-20 ethyleneoxy units.

3. A compound of item 1 or 2 wherein X is a biomolecule comprising a fluorophore and Z is a nucleotide or a polynucleotide both of which are optionally substituted with a label or a solid support.

4. A compound of item 1 to 3 wherein X is an acid labile protecting group and Z is a reactive linking group of the formula (IV):

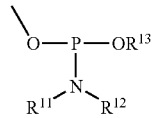

wherein R$^{11}$ and R$^{12}$ are individually selected from isopropyl, methyl, ethyl and C$_5$-C$_{14}$ aryl or R$^{11}$ and R$^{12}$ are, when taken together C$_4$-C$_{11}$ cycloalkyl or morpholino; R$^{13}$ is C$_1$-C$_6$ alkyl, substituted C$_1$-C$_6$ alkyl, C$_5$-C$_{14}$ aryl or a protecting group.

5. A compound of item 4 wherein R$^{11}$ and R$^{12}$ are both isopropyl and R$^{13}$ is cyanoethyl.

6. A compound of item 4 or 5 wherein X is a protecting group selected from the group consisting of DMT, MMT, trityl, substituted trityl, pixyl and trialkylsilyl.

7. A compound of items 1-6 wherein Z is a structure of the formula (V):

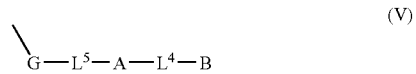

wherein A is a cleavable linker selected from the structures (Va-Vf):

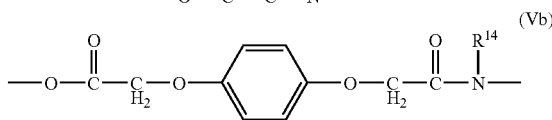

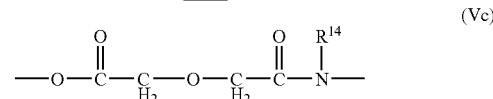

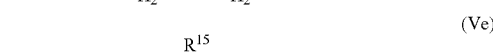

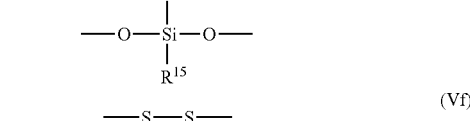

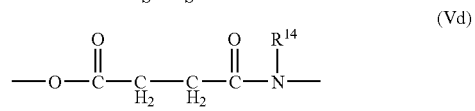

wherein R$^{14}$ is C$_{1-12}$ alkyl or C$_{1-12}$ alkoxy; R$^{15}$ is alkyl, aryl, arylalkyl or alkoxy; L$^4$ and Ls are independently selected from a bond or a linker selected from C$_1$-C$_{12}$-alkyldiyl, C$_1$-C$_{12}$-alkoxydiyl, C$_1$-C$_{12}$-alkylaminodiyl, C$_1$-C$_{12}$-alkylamidedlyl, aryldiyl or 1-20 ethyleneoxy units; G is a bond, a nucleotide, a substituted nucleotide, a polynucleotide, a substituted polynucleotide or a hybridization-stabilizing moiety; and B is a solid support.

8. A compound of item 7 wherein G comprises:

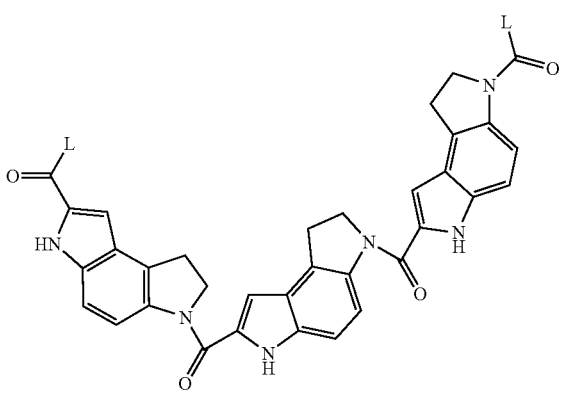

wherein L designates the sites of attachment to L$^2$ and L$^5$.

9. A compound of item 7 or 8 wherein the solid support is selected from polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of such.

10. A compound of item 7 or 8 wherein the form of the solid support is selected from a particle, a bead, a membrane, a frit, a fiber, a tube, a capillary, a slide, a plate, a micromachined chip, an alkanethiol-gold layer, a magnetic bead, a non-porous surface, an addressable array, and polynucleotide-immobilizing medium.

11. A compound of items 1-10 wherein X is a polynucleotide comprising a fluorescent dye.

12. A compound of item 11 wherein the polynucleotide comprises one or more N-[2-(aminoethyl)]glycine units having a nucleobase attached to nitrogen through a methylene carbonyl linkage.

13. A compound of item 11 wherein the polynucleotide comprises one or more of 2'-4' or 3'-4' bicyclic sugar modifications.

14. A quencher compositions of the formula (III):

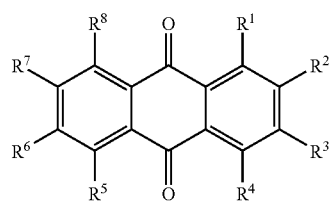

(III)

wherein $L^1$ and $L^2$ are each, independently, a bond or a linker; X is a biomolecule, a protected form thereof or an acid-labile or base labile protecting group; wherein the biomolecule is selected from an amino acid, a polypeptide, a nucleoside, a nucleotide or a polynucleotide and optionally further comprises a fluorophore; Z is a bond or selected from —H, —CO$_2$H, —OH, —NH$_2$, —NHR$^{10}$, or —N(R$^{10}$)$_2$, —SH, a phosphate, a nucleotide, a substituted nucleotide, a polynucleotide, a substituted polynucleotide, an ester, a cleavable linker, a solid support, a reactive linking group or a label; all of which are optionally substituted with a label or a solid support; and wherein $R^{10}$ is hydrogen, $C_1$-$C_6$ alkyl, aryl, aryldiyl, aryltriyl; Q is a compound of the formula (I)

(I)

wherein at least one, two, three or four of $R^1$, $R^4$, $R^5$ or $R^8$ are each and independently selected from substituted or non-substituted amino-alkyl, amino-aryl or amino-alkylaryl and the remaining $R^1$ to $R^8$ groups are each and independently hydrogen or substituted or non-substituted hydroxy, amino, alkyl, aryl, arylalkyl or alkoxy; and wherein Q is attached to the linkers $L^1$ and $L^2$ at two different positions, either through one of the α-amino groups or through the aryl carbons of the quencher moiety.

15. A compound of item 14 wherein $L^1$ and $L^2$ are each, independently, a bond or a linker selected from alkylaryl, $C_1$-$C_{12}$-alkyldiyl, $C_1$-$C_{12}$-alkoxydiyl, $C_1$-$C_{12}$-alkylaminodiyl, $C_1$-$C_{12}$-alkylamidedlyl, aryldiyl or 1-20 ethyleneoxy units.

16. A compound of item 14 or 15 wherein X is a biomolecule comprising a fluorophore and Z is a nucleotide or a polynucleotide both of which are optionally substituted with a label or a solid support.

17. A compound of items 14 to 16 wherein X is an acid labile protecting group and Z is a reactive linking group of the formula (IV):

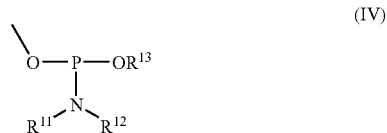

(IV)

wherein $R^{11}$ and $R^{12}$ are individually selected from isopropyl, methyl, ethyl and $C_5$-$C_{14}$ aryl or $R^{11}$ and $R^{12}$ are, when taken together $C_4$-$C_{11}$ cycloalkyl or morpholino; $R^{13}$ is $C_1$-$C_6$ alkyl, substituted $C_1$-$C_6$ alkyl, $C_5$-$C_{14}$ aryl or a protecting group.

18. A compound of item 17 wherein $R^{11}$ and $R^{12}$ are both isopropyl and $R^{13}$ is cyanoethyl.

19. A compound of item 17 or 18 wherein X is a protecting group selected from the group consisting of DMT, MMT, trityl, substituted trityl, pixyl and trialkylsilyl.

20. A compound of items 14 to 19 wherein Z is a structure of the formula (V):

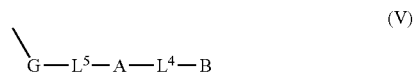

(V)

wherein A is a cleavable linker selected from the structures (Va-Vf):

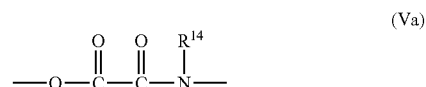

(Va)

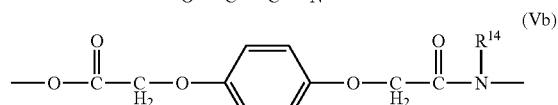

(Vb)

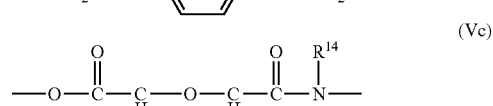

(Vc)

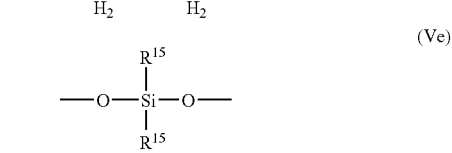

(Ve)

(Vf)

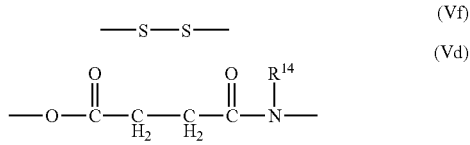

(Vd)

wherein $R^{14}$ is $C_{1-12}$ alkyl or $C_{1-12}$ alkoxy; $R^{15}$ is alkyl, aryl, arylalkyl or alkoxy; $L^4$ and $L^5$ are independently selected from a bond or a linker selected from $C_1$-$C_{12}$-alkyldiyl, $C_1$-$C_{12}$-alkoxydiyl, $C_1$-$C_{12}$-alkylaminodiyl, $C_1$-$C_{12}$-alkylamidediyl, aryldiyl or 1-20 ethyleneoxy units; G is a bond, a nucleotide, a substituted nucleotide, a polynucleotide, a substituted polynucleotide or a hybridization-stabilizing moiety; and B is a solid support.

21. A compound of item 20 wherein G comprises:

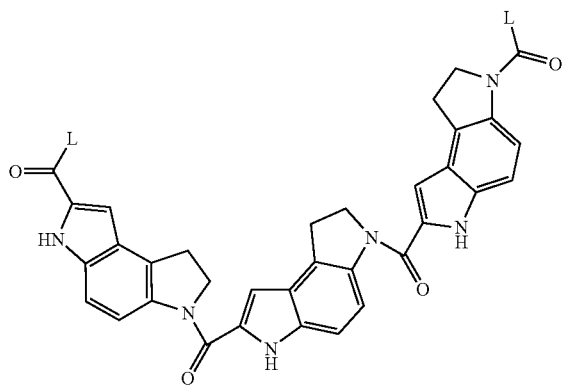

wherein L designates the sites of attachment to $L^2$ and $L^5$.

22. A compound of item 20 or 21 wherein the solid support is selected from polystyrene, controlled-pore-glass, silica gel, silica, polyacrylamide, magnetic beads, polyacrylate, hydroxyethylmethacrylate, polyamide, polyethylene, polyethyleneoxy, and copolymers and grafts of such.

23. A compound of item 20 or 21 wherein the form of the solid support is selected from a particle, a bead, a membrane, a frit, a fiber, a tube, a capillary, a slide, a plate, a micromachined chip, an alkanethiol-gold layer, a magnetic bead, a non-porous surface, an addressable array, and polynucleotide-immobilizing medium.

24. A compound of items 14 to 23 wherein X is a polynucleotide comprising a fluorescent dye.

25. A compound of item 24 wherein the polynucleotide comprises one or more N-[2-(aminoethyl)]glycine units having a nucleobase attached to nitrogen through a methylene carbonyl linkage.

26. A compound of item 24 wherein the polynucleotide comprises one or more of 2'-4' or 3'-4' bicyclic sugar modifications.

27. A compound of items 1 to 26 wherein Q is 1,8-bis-(3-hydroxy-propylamino)-anthraquinone or 1,5-bis-(3-hydroxy-propylamino)-anthraquinone.

28. A compound selected from 1,8-bis-(3-hydroxy-propylamino)-anthraquinone or 1,5-bis-(3-hydroxy-propylamino)-anthraquinone.

29. A polynucleotide probe containing at least one quencher composition according to any of the items 1-27.

30. A polynucleotide probe according to item 29 further comprising at least one quenchable label.

31. A polynucleotide probe according to item 30 wherein the quenchable label is separated from the quencher by a nuclease susceptible site.

32. A polynucleotide probe according to item 30 where the probe can adopt at least 1 conformation when not bound to the target where the label is quenched by the quencher, and at least one other conformation when the probe is bound to the target where the label is at least partially unquenched by the quencher.

33. A polynucleotide according to item 32, where a 3' part and a 5' part of the polynucleotide are perfectly complementary such as to form a hairpin structure when not bound to the target.

34. A polynucleotide probe according to any of the items 29 to 33, comprising at least one target recognition region complementary to a target gene.

35. A polynucleotide of any of the items 29 to 34 having a length of 5 to 50 nucleotides.

36. A polynucleotide probe according to item 31 where the probe is blocked for extension by the polymerase in the 3'end.

37. A method of primer extension comprising: annealing a polynucleotide primer to a target polynucleotide; and extending the primer by polymerase-mediated incorporation of a nucleotide 5'-triphosphate; wherein the primer or the nucleotide 5'-triphosphate is attached to a quencher moiety of the formula (I); whereby a labelled polynucleotide is formed.

38. The method of item 37 further comprising amplifying the target polynucleotide with nucleotide 5'-triphosphates, a polymerase, and two or more primers; wherein the primers are complementary to the target polynucleotide sequence and at least one primer is attached to a quencher moiety of the formula (I).

39. A method of amplifying a target polynucleotide comprising nucleotide 5'-triphosphates, a polymerase, two or more primers; wherein the primers are complementary to the target polynucleotide sequence, and a detectably labelled probe; wherein at least a part of the detectably labelled probe is complementary to the target polynucleotide and comprise at least a fluorescent dye and a quencher moiety of the formula (I).

40. The method of item 39 further comprising detecting a signal from the fluorescent dye of said detectable probe.

41. The method of item 40 wherein the signal is detected at each thermal cycle during amplification.

42. The method of item 39 wherein said polymerase cleaves the detectable probe during amplification; whereby the fluorescent dye and the quencher moiety are separated.

43. The method of item 42 further comprising detecting a signal from the fluorescent dye of said cleaved, detectable probe.

44. The method of item 43 wherein the signal is detected at each thermal cycle during amplification.

45. The method of item 39 wherein said fluorescent dye is attached to the 5' terminus or 3' terminus of the detectable probe.

46. The method of item 39 wherein said quencher moiety is attached to the 5' terminus or 3' terminus of or internally in the detectable probe.

47. The method of item 39 wherein the detectable probe is further labelled with a hybridization-stabilizing moiety.

48. The method of item 47 wherein the hybridization-stabilizing moiety comprises the structure:

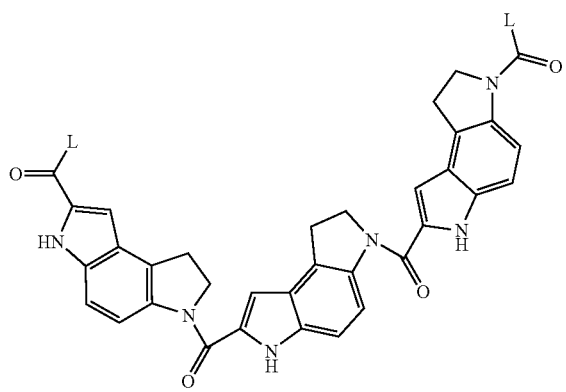

where L is an attachment site to the detectable probe.

49. A method of item 39 where the detectable probe has a format selected from molecular beacons, scorpion probes, sunrise probes, conformationally assisted probes and TaqMan probes.

50. A method of item 39 where the detectable probe comprises one or more one or more N-[2-(aminoethyl)]glycine units having a nucleobase attached to nitrogen through a methylene carbonyl linkage.

51. A method of item 39 wherein the detectable probe comprises one or more of 2'-4' or 3'-4' bicyclic sugar modifications.

52. A kit for nucleic acid amplification comprising two or more primers, and a probe with a detectable label and a quencher moiety of the formula (I).

53. A method of hybridization detection comprising annealing a probe to a target polynucleotide sequence, wherein the probe is covalently attached to a fluorescent dye and a quencher moiety of the formula (I); and detecting a signal from the fluorescent dye.

54. A kit for primer extension comprising one or more nucleotide 5'-triphosphates and one or more primers wherein at least one primer is covalently attached by a linkage to an aryl carbon of a quencher moiety of the formula (I).

55. A microarray comprising a quencher moiety of the formula (I) said quencher being conjugated directly to a solid support or to a carrier molecule attached to said solid support.

56. A method of probing a microarray for the presence of a compound, said method comprising: (a) contacting said microarray with a probe interacting with said compound, said probe comprising a quencher moiety of the formula (I); (b) detecting a difference in a fluorescence property of a member selected from said probe, said compound and combinations thereof, thereby ascertaining the presence of said compound.

57. A detection system comprising: (a) a target binding entity, (b) a quenchable detectable label and (c) a quencher according to any of items 1-27 wherein the quenchable label and the quencher each are positioned on the target binding entity and/or the target such that the label is quenched by the quencher when the target binding entity is unbound to its target, and such that binding of the binding entity to its target will remove the quencher from the label such that the label is at least partially unquenched.

58. A detection system comprising: (a) a target binding entity, (b) a quenchable detectable label and (c) a quencher according to any of items 1-27 wherein the quenchable label and the quencher each are positioned on the target binding entity and/or the target such that the label is at least partially unquenched by the quencher when the target binding entity is unbound to its target, and such that binding of the binding entity to its target will bring the quencher in vicinity of the label such that the label is at least partially quenched.

59. A detection system according to item 57 and 58 wherein the target binding entity comprises a polynucleotide, an antibody, an aptamer, or a ligand.

The invention claimed is:

1. A quencher composition of the formula (III):

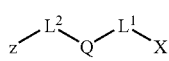

wherein $L^1$ and $L^2$ are each, independently a bond or a linker;
X is a polynucleotide comprising a fluorescent dye;
Z is a nucleotide or a polynucleotide both of which are optionally substituted with a label or a solid support;
Q is a compound of the formula (I)

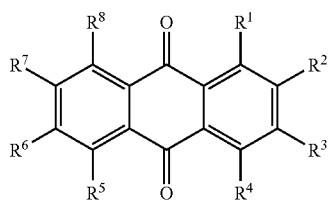

wherein at least one, two, three or four of $R^1$, $R^4$, $R^5$ or $R^8$ are each, independently selected from substituted or non-substituted amino-alkyl, amino-aryl and amino-alkylaryl, and the remaining $R^1$ to $R^8$ groups are each, independently hydrogen or substituted or non-substituted hydroxy, amino, alkyl, aryl, arylalkyl or alkoxy; and wherein Q is attached to the linkers $L^1$ and $L^2$ at two different positions, either through one of the α-amino-groups or through the aryl carbons of the quencher moiety.

2. A quencher compositions of the formula (III):

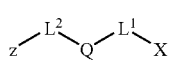

wherein $L^1$ and $L^2$ are each, independently a bond or a linker;
X is a biomolecule or a protected form thereof, or an acid-labile or base labile protecting group;
wherein the biomolecule is selected from an amino acid, a polypeptide, a nucleoside, a nucleotide and a polynucleotide, and optionally further comprises a fluorophore;
Z is selected from —$CO_2H$, —SH, a phosphate, a nucleotide, a substituted nucleotide, a polynucleotide, a substituted polynucleotide, an ester, a cleavable linker, a solid support, and a label;
all of which are optionally substituted with a label or a solid support;
and wherein $R^{10}$ is selected from $C_1$-$C_6$ alkyl, and aryl, Q is a compound of the formula (I)

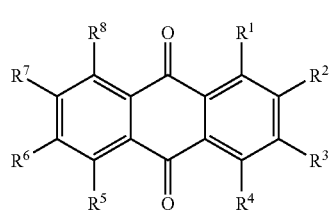

wherein at least one, two, three or four of $R^1$, $R^4$, $R^5$ or $R^8$ are each, independently selected from substituted or non-substituted amino-alkyl, amino-aryl and amino-alkylaryl, and the remaining $R^1$ to $R^8$ groups are each, independently hydrogen or substituted or non-substituted hydroxy, amino, alkyl, aryl, arylalkyl or alkoxy; and wherein Q is attached to the linkers $L^1$ and $L^2$ at two different positions, either through one of the α-amino-groups or through the aryl carbons of the quencher moiety.

3. The quencher composition according to any one of claims 1 and 2, wherein Q is selected from 1,4-bis-(3-hydroxy-propylamino)-anthraquinone (1), 1,5-bis-(3-hydroxy-propylamino)-anthraquinone (4), 1,4-bis-(4-(2-hydroxy-ethyl)phenylamino)-anthraquinone (7), and 1,8-bis-(3-hydroxy-propylamino)-anthraquinone.

4. A quencher composition according to any one of claims 1, 2, and 3, wherein X is a polynucleotide comprising a fluorescent dye, wherein the polynucleotide comprises one or more of 2'-4' or 3'-4' bicyclic sugar modifications.

* * * * *